(12) United States Patent
Ullakko et al.

(10) Patent No.: US 9,091,251 B1
(45) Date of Patent: Jul. 28, 2015

(54) ACTUATION METHOD AND APPARATUS, MICROPUMP, AND PCR ENHANCEMENT METHOD

(75) Inventors: Kari Ullakko, Savolinna, FL (US); Peter Mullner, Boise, ID (US); Greg Hampikian, Boise, ID (US); Aaron Smith, Meridian, ID (US)

(73) Assignee: Boise State University, Boise, ID (US)

( * ) Notice: Subject to any disclaimer, the term of this patent is extended or adjusted under 35 U.S.C. 154(b) by 49 days.

(21) Appl. No.: 13/550,386

(22) Filed: Jul. 16, 2012

Related U.S. Application Data

(60) Provisional application No. 61/507,991, filed on Jul. 14, 2011, provisional application No. 61/560,603, filed on Nov. 16, 2011.

(51) Int. Cl.
*G01N 21/75* (2006.01)
*F03G 7/06* (2006.01)
*F04B 17/00* (2006.01)

(52) U.S. Cl.
CPC ............... *F03G 7/065* (2013.01); *F04B 17/00* (2013.01); *G01N 21/75* (2013.01)

(58) Field of Classification Search
CPC ..................................................... G01N 21/75
USPC ........................................................ 422/417
See application file for complete search history.

(56) References Cited

U.S. PATENT DOCUMENTS

| | | | |
|---|---|---|---|
| 6,074,179 A | 6/2000 | Jokela et al. | |
| 6,515,382 B1 * | 2/2003 | Ullakko | 310/26 |
| 6,633,100 B2 * | 10/2003 | Sato et al. | 310/152 |
| 7,710,766 B2 | 5/2010 | Mullner et al. | |
| 7,964,290 B2 | 6/2011 | Mullner et al. | |
| 8,008,806 B2 | 8/2011 | Day | |
| 2007/0298423 A1 * | 12/2007 | Remacle et al. | 435/6 |
| 2011/0064965 A1 | 3/2011 | Mullner et al. | |
| 2011/0110139 A1 | 5/2011 | Mullner et al. | |

OTHER PUBLICATIONS

Ullakko, K., et al; "Large Magentic-Field-Induced Strains in Ni2MnGa Single Crystals;" Applied Physics Letters 69, 1966-1968 (1996).
Dunand, D.C. & Mullner, P., "Size Effects on Magnetic Actuation in Ni—Mn—Ga Shape-Memory Alloys," Advanced Materials 23, pp. 216-232; 2011.
Hatch, A., Kamholz, A.E. Holman, G., Yager, P. & Bohringer, K.F., "A ferrofluidic magnetic micropump;" Journal of Microelectromechanical Systems, vol. 10., pp. 215-221; 2001.
Laser, D.J. & Santiago, J.G.; "A review of micropumps;" Journal of Micromechanics and Microengineering; vol. 14, R35; 2004.
Nespoli, A., Besseghini, S., Pittaccio, S., Villa, E. & Viscuso, S.; "The high potential of shape memory alloys in developing miniature mechanical devices: A review on shape memory alloy mini-actuators;" Sensors and Actuators A: Physical; vol. 158, pp. 149-160; 2010.
Smits, J.G.; "Piezoelectric micropump with three valves working peristaltically;" Sensors and Actuators A: Physical; vol. 21, pp. 203-209; 1990.

* cited by examiner

*Primary Examiner* — Ardin Marschel
(74) *Attorney, Agent, or Firm* — Parsons Behle & Latimer

(57) ABSTRACT

An actuation apparatus includes at least one magnetic shape memory (MSM) element containing a material configured to expand and/or contract in response to exposure to a magnetic field. Among other things, the MSM element may be configured to pump fluid through a micropump by expanding and/or contracting in response to the magnetic field. The magnetic field may rotate about an axis of rotation and exhibit a distribution having a component substantially perpendicular to the axis of rotation. Further, the magnetic field distribution may include at least two components substantially orthogonal to one another lying in one or more planes perpendicular to the axis of rotation. The at least one MSM element may contain nickel, manganese, and gallium. A polymerase chain reaction (PCR) may be enhanced by contacting a PCR reagent and DNA material with the MSM element.

27 Claims, 16 Drawing Sheets

ACTUATION METHOD AND APPARATUS, MICROPUMP, AND PCR ENHANCEMENT METHOD

RELATED APPLICATION DATA

The present application claims the benefit of priority under 35 U.S.C. §119 to U.S. Provisional Application No. 61/507,991 filed Jul. 14, 2011, entitled "Apparatus for Multi-Axial Actuation," and U.S. Provisional Application No. 61/560,603 filed Nov. 16, 2011, entitled "Micropump and PCR Enhancement Method," both of which are incorporated herein by reference.

GOVERNMENT LICENSE RIGHTS

This invention was made with government support under grant no. DEFG-02-07ER46396 awarded by the Department of Energy (DOE); and under grant no. IF11-004 awarded by HERC. The government has certain rights in the invention.

TECHNICAL FIELD

The embodiments herein relate to apparatuses for making shape changes in magnetic shape memory materials using a rotating permanent magnet, micropumps, and polymerase chain reaction (PCR) enhancement methods.

BACKGROUND

The lab-on-a-chip revolution has produced a number of innovations that herald a new age of portable field instruments and point of care diagnostics. Micro total analysis systems (αTAS) incorporate a variety of traditional material such as glass and silicone, but other materials are now being widely adopted, such as ceramics and sapphire, as well as polymers such as polydimethylsiloxane (PDMS), polymethylmethacrylate (PMMA), polycarbonate (PC), and cyclic olefins. Many functional components for these miniaturized devices have been developed for biological testing including homogenizers, cell disruptors, antigen binders, laser detectors, heaters, electrophoretic separators, mobility analyzers etc. and there is a trend toward self-contained disposable chips for clinical use.

Less development has occurred in the area of micropumps, with many devices still being driven by external traditional peristaltic pumps or syringes. Development has occurred for piezoelectric, lithographic, ferromagnetic fluid, acoustic wave, and polymeric pumps, but there is still large room for improvement in terms of a component-based chip technology. In such technology, pumps can be manufactured along with the chips and placed throughout the chip architecture.

U.S. Pat. No. 6,074,179 issued to Jokela describes a magnetostrictive peristaltic pump using Terfenol-D material, which can be made to expand directionally in the presence of a magnetic field. However, Jokela uses electric coils with positive and the negative terminals connected to a signal generator to expand the Terfenol-D material longitudinally and move fluid through the device. The Jokela pump is not adapted to provide the desirable features of micropumps.

SUMMARY

In an embodiment, an actuation method includes rotating a magnetic field about an axis of rotation, the magnetic field exhibiting a distribution having a component substantially perpendicular to the axis of rotation. At least one MSM element is exposed to different portions of the magnetic field distribution as a result of rotating the magnetic field. The method includes contracting and/or expanding the MSM element in response to exposure to the perpendicular component of the magnetic field distribution.

In another embodiment, an actuation apparatus includes at least one magnetic field generator exhibiting a magnetic field distribution. A magnetic field alignment device is configured to restrain magnetic field movement to rotation about an axis of rotation, the magnetic field distribution having a component substantially perpendicular to the axis of rotation. At least one MSM element contains a material configured to contract and/or expand in response to exposure to the perpendicular component of the magnetic field distribution.

In a further embodiment, a micropump includes at least one MSM element containing a material configured to expand and/or contract in response to exposure to a magnetic field. A device is configured to generate a magnetic field, the MSM element being configured to pump fluid through the micropump by expanding and/or contracting in response to the magnetic field.

In a still further embodiment, a PCR enhancement method includes using a PCR reagent combined with a DNA material and contacting the PCR reagent and DNA material with a magnetic shape memory (MSM) element. The method includes amplifying the DNA material, the amplification being greater than would occur in the method without the PCR reagent and DNA material contacting the MSM element.

BRIEF DESCRIPTION OF THE DRAWINGS

Some embodiments are described below with reference to the following accompanying drawings.

DETAILED DESCRIPTION

Magnetically controlled Shape Memory (MSM) alloys develop strains of several percent when a magnetic field is applied to them. Those materials can be used as strain sensors, vibration dampers and electric power generators. Strains in apparatus components made from MSM alloys, hereafter "MSM elements," are based on magnetic-field-induced changes of the proportions of twin variants. The main group of the MSM materials is Ni—Mn—Ga alloys. MSM materials exhibit an enormous commercial potential due to their large and precise strokes at high speeds. MSM materials are expected to replace electromagnetic machines, solenoids and piezo ceramic actuators in many applications. In part, the embodiments herein relate to apparatuses for actuating different parts of an MSM element locally using a permanent magnet that generates a magnetic field distribution with magnetic field components of different directions at the same time, thus creating local shape changes in the directions that lie in the plane perpendicular to the rotating axis of the magnet.

An apparatus for producing local strains in different parts of the element simultaneously in an MSM element by means of a magnetic field distribution may function by a rotating diametrically magnetized cylindrical permanent magnet placed on a side of the MSM element. The magnet can be a circular rod or a disc or any other suitable configuration. The strains are produced by the substantially orthogonal magnetic field components that lie in the plane perpendicular to the rotating axis, i.e., the symmetry axis, of the cylindrical magnets. The local strains occur in the plane perpendicular to the rotating and symmetry axis of the magnet.

The strains can be contraction, elongation or shear, or any combination of them. When the magnet rotates, the strains vary, accordingly. The rotation of the magnet can be of any angle or full turns in both directions. The magnetic circuit may also contain a yoke to orient the magnetic field distribution. The yoke may be placed in the same side of the element as the magnet, or partially or wholly on the other side of the element, or lateral to the element or in extension of the element.

Figure 1:
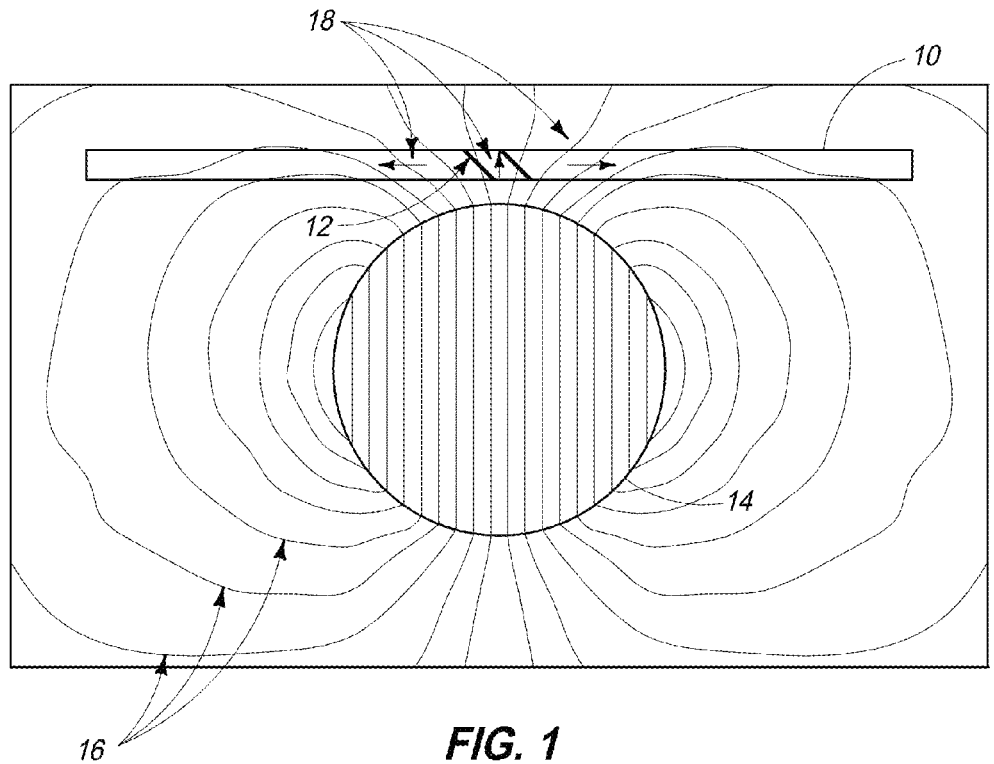
FIG. 1 shows magnetic flux lines calculated for 10M martensitic structure of Ni—Mn—Ga alloy produced by a diametrically magnetized iron-boron-neodymium magnet.

The magnetic field components generated by the rotating magnet onto the MSM element may exhibit sufficiently high magnetic field energies with respect to the magnetocrystalline anisotropy energy of the MSM material for turning the crystallographic axis corresponding to the easy direction of magnetization of the MSM material from one crystallographic direction to another. FIG. 1 shows a magnetic field distribution 16 in a MSM element 10 made from a Ni—Mn—Ga alloy that exhibits a 10M martensitic structure produced by a diametrically magnetized cylindrical iron-boron-neodymium magnet 14. A shrinkage 12 is about 1 millimeter (mm) in the length direction of the element. The magnetic field components lie in the plane perpendicular to the rotating and symmetry axis of the magnet. The magnetic field components are substantially perpendicular to each other, as shown by arrows 18 in FIG. 1. The magnetic field changes gradually between the two directions. A more detailed description is found below.

The general principles may be illustrated through various embodiments. For ease of illustration only, assume that the easy direction of magnetization of the MSM material is parallel to the crystallographic direction of the shortest lattice parameter, another crystallographic direction is magnetically hard, and the lattice parameter in the hard direction is larger than that of the easy direction. If a magnetic field component of sufficiently high field strength is directed along the direction of the larger lattice parameter in a certain section of the MSM element, the lattice shrinks in that section and the previous hard magnetic direction becomes the easy direction in that section of the element.

Also for purposes of illustration only, assume further that the MSM element contains two substantially orthogonal crystallographic directions whose lattice parameters are a and c, the c axis being the shorter axis. Such a material can be, for example, the 10M martensite of Ni—Mn—Ga alloys. In this example, the c axis is the easy direction of magnetization of the material. The material shrinks in the direction of the magnetic field if the magnetic field component in the c direction is sufficiently high. If the magnetic field distribution in the MSM element contains two such components of sufficiently high field strength directed substantially perpendicular to each other, the element exhibits shrinkage. When the components are varied in time by rotating the permanent magnet, the shrinkage moves along the MSM element. Because the two magnetic field directions are perpendicular and parallel to a horizontally placed rectangular element, correspondingly, the shrinkage appears in those sections of the element in which the magnetic field is in perpendicular direction.

Figure 2:
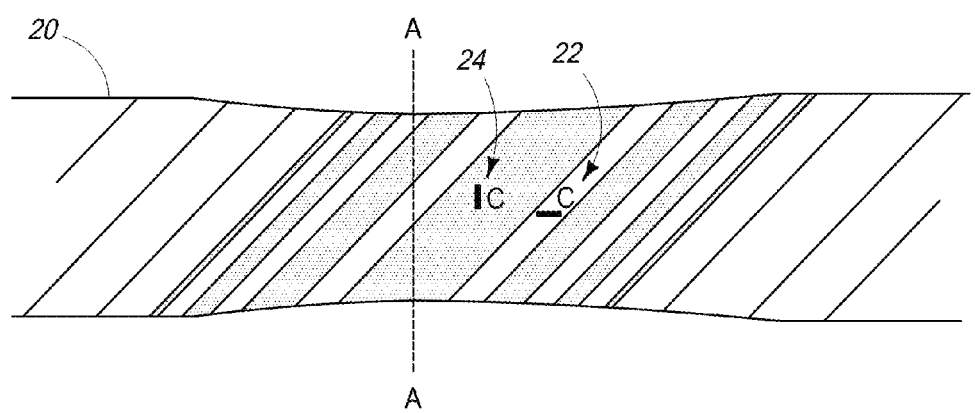
FIG. 2 shows a side view of twin structure in shrinkage of the FIG. 1 alloy.

FIG. 2 shows a side view of the twin structure in the shrinkage of a MSM element 20. The dark and light stripes in 45 degrees orientation are twin variants. The short lattice axis c (24) is directed in the vertical direction of the twin variants marked as dark, and the c axis (22) is directed in the horizontal direction in the other variants marked as light. The magnetic field component in the vertical direction increases the fraction of the dark variant, making the dark variants broader. Accordingly, the magnetic field component in the horizontal direction increases the fraction of the light variants. Thickness L of the sample at location A (see dashed line A-A in FIG. 2) can be expressed as:

$$L = f_c \times c + f_a \times a \qquad \text{(Equation 1)}$$

where $f_c$ and $f_a$ are the number of unit cells of lattice parameters c and a, correspondingly, in the vertical cross section of the shrinkage at location A.

When the magnet rotates, the shrinkage travels along the element. Because the volume of the Ni—Mn—Ga sample remains substantially constant, the sample expands in the horizontal direction in the shrinkage area. If the element is not fixed, and it is in contact to at least one surface that exhibits a sufficient friction, the element moves in relation to the surface when the shrinkage moves. A linear motor may be based on this principle as discussed below.

Figure 3:
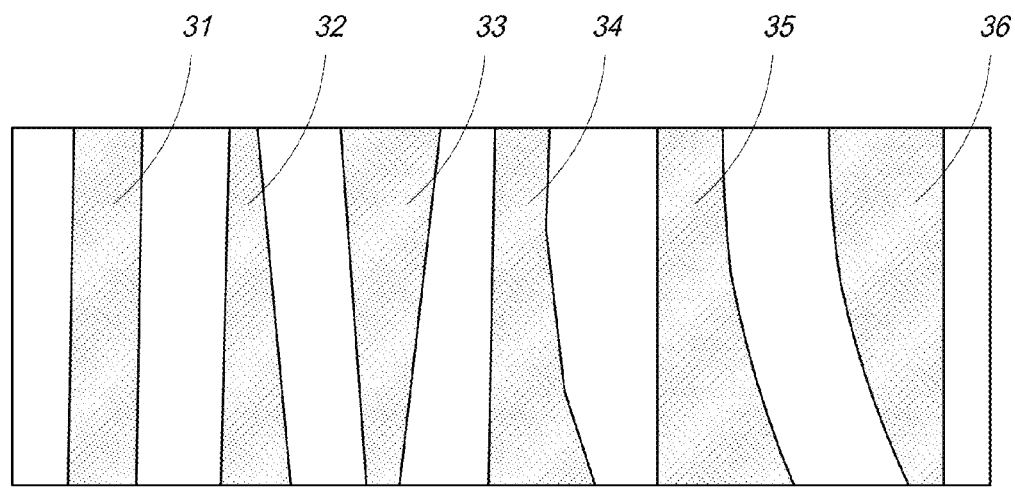
FIG. 3 shows top views of different shapes of shrinkages.

A shrinkage can also be negative, i.e. an expansion, if the easy direction, or the easy plane of magnetization, is along the long crystallographic axis. In non-layered martensite of Ni—Mn—Ga, there is an easy plane of magnetization. FIG. 3 shows examples of top views of shrinkages. FIG. 3 shows only the outer borders of the shrinkages schematically, and not the twin structures within the shrinkages. Although the MSM element is shown as rectangular for simplicity, the MSM element can be of many other shapes. Shrinkage 31 in FIG. 3 contains substantially parallel boundaries. Boundaries of shrinkages 32 and 33 are non-parallel. These types of shrinkages appear, for instance, in an element that is bent sidewise. In shrinkage 34, one boundary is composed of straight lines with different angles. Shrinkages 35 and 36 represent shrinkages with curved boundaries. The shrinkage can also be any combination of 1 to 6.

The magnet and the yoke can be placed on one side of the MSM element, or the magnet can be on one side of the element and the yoke on the other side. Rotation of the magnet produces a varying magnetic field distribution that changes the proportions of the two crystallographic variants. The magnetic field distribution in the element produced by the diametrically magnetized cylindrical magnet creates shrinkage in the element. When the magnet rotates, the shrinkage travels along the element.

In FIG. 1, shrinkage 12 is at a 45 degree angle following the twin plane direction. In the modeling that yielded FIG. 1, perpendicular flux lines were concentrated (0.85 Tesla) in the shrinkage area. Horizontal flux lines (density about 0.9 T) cover several millimeters along the MSM element in both sides of the shrinkage. The flux density calculations reveal that the vertical magnetic field component is sufficiently high in the shrinkage section to orient the short crystallographic axis c in the vertical direction, and at the same time the horizontal magnetic field component is high enough for orienting the c axis in the horizontal direction on both sides of the shrinkage.

Demonstrations showed that a diametrically magnetized cylindrical permanent magnet forms shrinkage in the 10M martensitic Ni—Mn—Ga element. Also the shrinkage travels along the element when the magnet rotates, in both directions. The experiments were made with cylindrical magnets of 6 mm and 2.5 mm in diameters.

Figure 4:
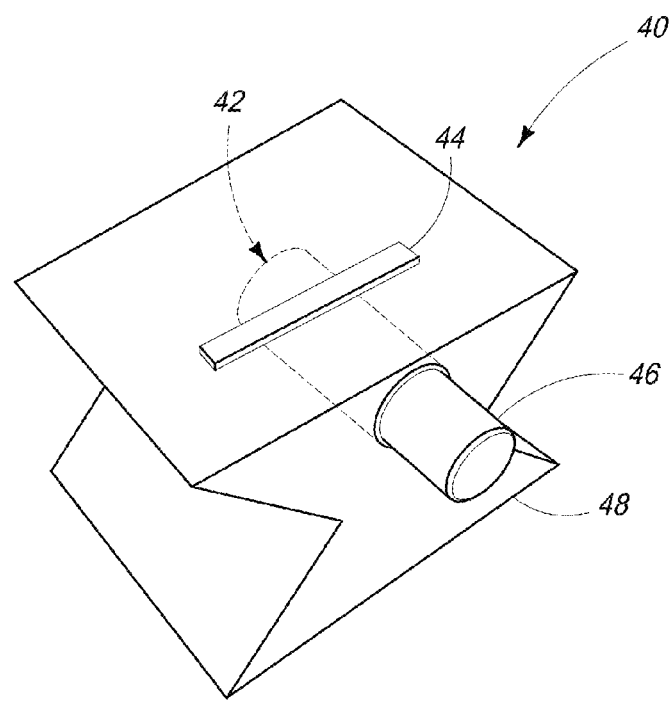
FIG. 4 is a perspective view of an apparatus for forming the shrinkage of FIG. 2.
Figure 7:
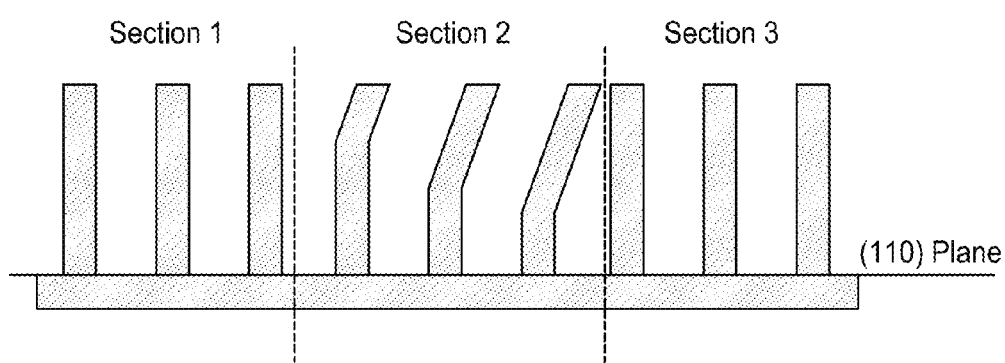
FIG. 7 shows a wave-like motion of the kinking of the MSM pillars when the magnetic field distribution generated by the rotating diametrically magnetized cylindrical magnet varies.

FIG. 4 shows a setup 40 for forming shrinkage 42 in an MSM element 44 and moving it by a cylindrical magnet 46 of 6 mm in diameter. FIG. 7 shows a side view of a similar apparatus in which the same reference numbers refer to the same parts of the apparatus, except that the diametric nature of the magnet is illustrated, with 46a and 46b being, for example, the north and south magnetic poles of the magnet, respectively. The plastic jig is noted by 48. In an example, the magnet produces a shrinkage of about 1 mm in length; and when the magnet rotates, the shrinkage moves along the element about 12 mm in both directions. The length of shrinkage and the amount of movement along the element can vary widely depending on the properties of the MSM element and the magnet used.

While the experiment was made with a cylindrical magnet, any suitable configuration or size of magnet could be employed, including rod or disc magnets, as long as the direction of the north and south poles of the magnets changes relative to the element. Further, the direction of rotation of the magnet can change as desired. The MSM element can comprise any type of magnetic shape memory material that exhibits twining. Examples include nickel manganese gallium alloys, such as $Ni_{51.3}Mn_{26.3}Ga_{22.4}$ or Ni-27Mn-23Ga (in atomic %). Other examples include iron palladium and iron platinum alloys.

In one example, shrinkage motion in a 10 mm long MSM element was demonstrated, when the magnet rotated as in the jig shown in FIG. 4. The shrinkage traveled from one end of the element to the other when rotating the magnet both clockwise and counterclockwise. The elongation of the sample in the direction of the long dimension of the element in the shrinkage section was also demonstrated.

Figure 5:
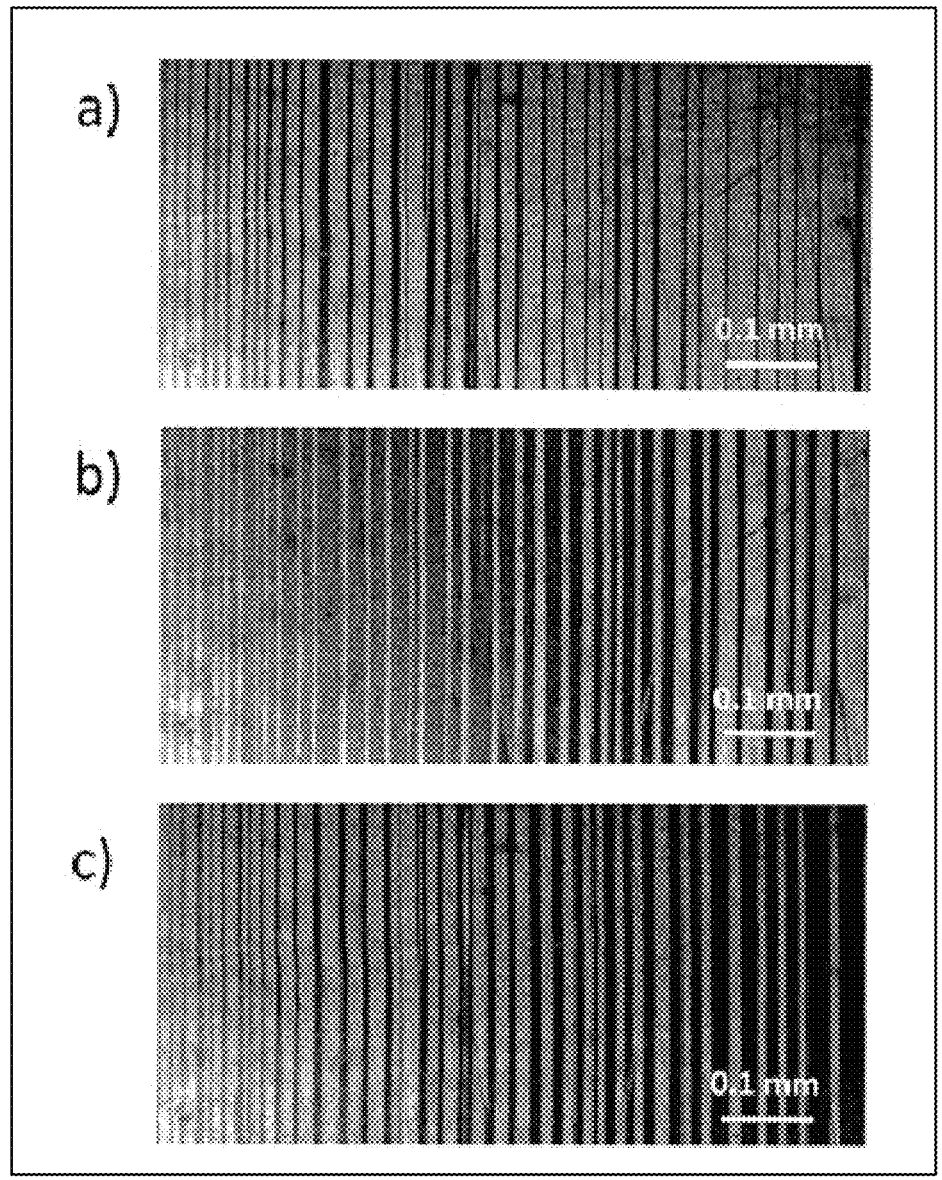
FIG. 5 shows micrographic snapshots of the twins, when the shrinkage driven by a rotating diametrically magnetized magnet of 6 mm in diameter travels across the view area from left to right.

FIG. 5 shows micrographic snapshots of the twins, when the shrinkage, driven by a rotating diametrically magnetized magnet of 6 mm in diameter, travels across the view area from left to right. FIG. 5 shows a top view of the MSM element where the twins are in 90 degrees orientation to the direction of the long dimension of the MSM element. FIG. 5a presents the twin structure just when the shrinkage starts reaching the view area from the left. The dark vertical stripes are twin variants whose short crystallographic axis c is perpendicular to the view surface and parallel to the shrinking direction. FIG. 5b represents the situation when the center area of the shrinkage has reached the view area. FIG. 5b shows gradually broadening twins (dark areas) from left to right. The left side of FIG. 5b shows broad dark twins indicating that this section of the MSM element has nearly fully shrunk. FIG. 5c shows the situation when the shrinkage has partially passed the view area. The tail of the shrinkage is composed of gradually broadening light twins from right to left, indicating that the MSM element is becoming thicker.

A demonstration using a Newton ring method showed that the two-axis magnetic field distribution generated by the diametrically magnetized cylindrical magnet produces shrinkage in the MSM element. A planar glass plate was placed on top of the MSM element. Newton rings appear due to an interference of light, if the distance between the glass surface and the MSM element surface is of the order of the wave length of light. A dark Newton ring appears as a destructive interference when the distance between the surfaces is a multiple of half the wave length of the light and a light ring appears as a constructive interference when the distance is a multiple of the light wave length. The Newton rings show the distance between the glass and the surface of the MSM samples in different locations of the sample at the same time.

Shrinkage was noted when rotating the diametrically magnetized cylindrical magnet of 6 mm in diameter beneath the MSM element. Newton rings appeared in the area adjacent the shrinkage, showing that the sample surface was very close to the glass surface. No Newton rings appeared in the shrinkage area, indicating that the distance between the surface of the MSM element and the glass plate was larger. This demonstration showed that the two-axis magnetic field distribution generated by the cylinder magnet forms shrinkage in the MSM element and that the shrinkage moves when the magnet rotates. The Newton rings also reveal the surface relief caused by individual twins.

Use of a similar device demonstrated an operating principle for a linear motor. A thin glass plate covered the MSM element and was held in place at a constant distance from a support block by screws. The magnet created a shrinkage that moved along the MSM element as the magnet rotated. The confinement imposed by the glass plate was believed to result in a force on the MSM element when the shrinkage moved. The force apparently pushed the MSM element resulting in a displacement of the entire element. Dimensions of the Ni—Mn—Ga sample were $1 \times 3 \times 20$ mm$^3$. The motion was about 2 mm in the longest dimension after 30 cycles of the shrinkage motion.

The embodiments herein exhibit application potential in several fields, such as optics, micro robotics, industrial automation and biotechnology. The applications of the embodiments are based on the motion of the shrinkage by rotating the diametrically magnetized cylindrical permanent magnet. The shape changes of the shrinkage can be extension, contraction, or shear. The shrinkages shown above are examples of extension and contraction.

A special case of shrinkage is a twin. In an unconstrained MSM element, the magnetic field distribution generated by the diametrically magnetized cylindrical magnet can produce a shrinkage that is a single twin variant. When the magnet rotates, the variant travels along the MSM element, as schematically shown in FIG. 5. The motion of the middle (tilted) section can be used, for instance, in optical applications for reflecting light.

Figure 6:
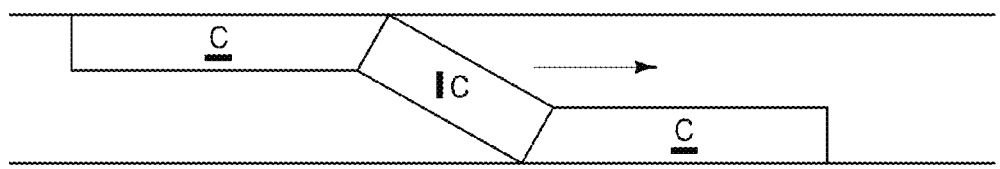
FIG. 6 shows schematically an example of a shrinkage moving from left to right when the diametrically magnetized cylindrical magnet rotates beneath the MSM element.

An example of the shear strains in the sections of the MSM element is shown in FIG. 6. A 10M martensitic Ni—Mn—Ga sample was cut along the (110) plane. Magnetic field directed in the (100) direction causes kinking of the section instead of contraction. FIG. 6 shows a wave-like motion of the kinking of the MSM pillars when the magnetic field distribution generated by the rotating magnet varies. This wave is an example of shear-type shrinkage. Motion in small biological organisms is mostly based on the same principle. When the magnetic field distribution shown in FIG. 6 moves along the MSM element from left to right, the wave moves, accordingly, from left to right. This wave-like motion can be applied in many technologies including micro manipulation, micro fluidics, drug delivery, micro transport and robotics.

MSM elements may include a material having two crystallographic variants exhibiting different crystallographic directions with different lattice parameters. The material may have magnetocrystalline anisotropy energy that is sufficient between those crystallographic directions with respect to the magnetic field energy acting upon the element to change the crystallographic orientations in different parts of the element simultaneously in response to substantially orthogonal magnetic field components. The easy direction of magnetization of the element material may be parallel to the crystallographic direction of the shortest lattice parameter. The element can shrink in the direction of the magnetic field in that section of the element in which the magnetic field is directed along the easy direction of the magnetization, and expand in another crystallographic direction in another part of the element.

In an embodiment, an actuation method includes rotating a magnetic field about an axis of rotation, the magnetic field exhibiting a distribution having a component substantially perpendicular to the axis of rotation. At least one MSM element is exposed to different portions of the magnetic field distribution as a result of rotating the magnetic field. The method includes contracting and/or expanding the MSM element in response to exposure to the perpendicular component of the magnetic field distribution.

By way of example, the contracting and/or expanding may occur locally in response to local exposure to the perpendicular component. The at least one MSM element may contain or consist of nickel, manganese, and gallium. Rotating the magnetic field may include rotating at least one permanent magnet. The magnetic field distribution may include at least two components substantially orthogonal to one another lying in one or more planes perpendicular to the axis of rotation and one of the orthogonal components may include the component substantially perpendicular to the axis of rotation.

The at least one MSM element may consist of one MSM element. The orthogonal components may lie in the same plane perpendicular to the axis of rotation. The MSM element may contract and/or expand in at least two different parts of the MSM element simultaneously in response to exposure simultaneously to the orthogonal components of the magnetic field distribution.

Alternatively, as discussed further below, the at least one MSM element may include a plurality of MSM elements, individual ones of the orthogonal components laying in different planes perpendicular to the axis of rotation. The MSM elements may contract and/or expand in different directions in response to exposure to the orthogonal components of the magnetic field distribution.

In another embodiment, an actuation apparatus includes at least one permanent magnet exhibiting a magnetic field distribution. A magnet alignment device is configured to restrain magnet movement to rotation about an axis of rotation, the magnetic field distribution having a component substantially perpendicular to the axis of rotation. At least one MSM element contains a combination of nickel, manganese, and gallium configured to contract and/or expand in response to exposure to the perpendicular component of the magnetic field distribution.

By way of example, the MSM element may be configured to contract and/or expand locally in response to local exposure to the perpendicular component. The at least one permanent magnet may include a diametrically magnetized magnet. The at least one permanent magnet may instead include a wheel mounted with at least six permanent magnets. The at least one permanent magnet may exhibit a magnetic field distribution having at least two components substantially orthogonal to one another lying in one or more planes perpendicular to the axis of rotation and having at least one of the orthogonal components also substantially perpendicular to the axis of rotation.

One application includes a micropump that essentially uses a single component, the MSM element. MSM Ni—Mn—Ga elements are relatively new materials with a variety of remarkable properties. They respond to changes in magnetic fields by elongating and shortening up to 6%. The pump can be driven by rotation of a cylindrical magnet, or by rotation of a magnetic field, it is reversible, and it can be operated by hand without any electrical power. The MSM element does not inhibit polymerase chain reaction, and may enhance it. Such a micropump was demonstrated to be compatible with forensic applications and shown to enhance human DNA profiling. The micropump may be suitable for lab-on-a-chip applications that use microfluidics.

One desirable feature of a micropump component for lab-on-a-chip applications is that it be free from electrical contacts and sealed within a potentially disposable lab-on-a-chip unit. Another desirable feature of a micropump is that the pump material itself would pump (akin to muscle fibers) and would be able to serve without ancillary mechanical devices. Finally, the pump may be both precise and sensitive over a wide range of volumes.

A pump is described herein matching these criteria and made of MSM Ni—Mn—Ga elements. Pump demonstrations showed that MSM may be used in biological testing, enhances polymerase chain reaction (PCR), and can be used to generate accurate forensic profiles using popular commercial kits (QUANTIFILER and IDENTIFILER available from Life Technologies Corp. in Carlsbad, Calif.).

EXAMPLE 1

Micropump Construction

Turning to FIG. 8, a pump 80 was built to fit the specifications of forensic DNA profiling (generally 1-20 microliter (μl) volumes) and to be capable of precisely delivering the solutions used in these reactions: DNA in water, or complete profiling reactions with polymerase, nucleotides, genomic DNA, Magnesium, buffers, and all the components of the manufacturer's kit. The pump was made of a Ni—Mn—Ga single crystal serving as MSM element, suspended in an elastic resin 82, and covered with a glass slide 83 which was glued to the element (with epoxy 84) at its ends. Two holes 85 (1 mm in diameter) were previously drilled into the glass slide as inlet and outlet.

Magnetic shape memory $Ni_{51.3}Mn_{26.3}Ga_{22.4}$ (numbers indicate atomic percent, nominal composition) single crystals were grown via a modified Bridgman method using an oriented seed crystal aligned with $<100>_c$ parallel to the growth direction. The composition was chosen such as to provide the 10M martensite structure and a very low twinning stress.

Two 1 mm diameter holes were cut into the glass microscope slides with a distance of 4 mm from the center of each hole. The glass slide was then cut using a diamond impregnated wafer saw so the dimensions were 25 mm×10 mm×1 mm. Ethanol was used to clean the surface of the glass to ensure there were no particles that could interfere with the bonding of the elastomer or the working surfaces of the Ni—Mn—Ga.

The working mechanism of the MSM micropump was the Ni—Mn—Ga element. The MSM element was cut from the Ni—Mn—Ga single crystal using a wire saw (50 micrometer (μm) diameter wire) so that the overall dimensions were 20 mm×2.5 mm×1 mm. To relieve surface stresses caused by cutting, the sample was then electropolished using a chilled solution consisting of 40 milliliters (ml) of ethanol and 20 ml of 16M nitric acid. After compressing the MSM element so that it was in a single martensite variant state, it was then electropolished four times for five second intervals at twelve volts. The MSM element was rinsed after each interval with a chilled sodium bicarbonate solution to cool the element and neutralize the acid.

The working surface of the MSM micropump warranted special attention to make certain that the pump was sealed. Consequently, one surface of the MSM element was mechanical polished to ensure that it was planar. A 9 μm, 3 μm then 1 μm polishing slurry was used in conjunction with a polishing wheel and a polishing jig for five minutes at each interval. The MSM element and polishing jig were rinsed thoroughly with distilled water between each step to ensure there was no particulate contamination.

After the MSM element had been polished, it was carefully cleaned with ethanol and then compressed into a short, single phase and placed on a fixture with a rotatable, diametrically magnetized, cylindrical N52 permanent magnet (available from K&J Magnetics, Inc.) beneath it.

Using the perpendicular magnetic field from the diametrically magnetized, cylindrical magnet, a second phase was introduced into the middle of the MSM element that was approximately 1 mm in length. Without this alternate, long phase in the MSM element, the micropump might have been unable to transfer liquid from inlet to outlet.

Figure 8A:
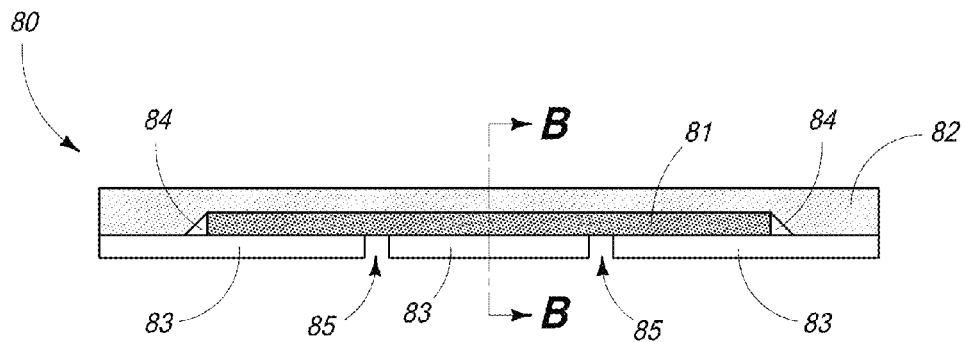
FIGS. 8A and 8B are sectional views of a micropump.

Two part all-purpose epoxy (DEVCON available from ITW Devcon in Danvers, Mass.) was used to fix and constrain both ends of the MSM element onto the prepared glass slide (FIG. 8A). It was beneficial to align the center of the MSM element, both its length and width, to the two holes while leaving the intermediate, long variant undisturbed. While the epoxy was hardening, low pressure was applied to the back of the MSM element to make sure there was complete surface-to-surface contact between the glass and element.

Figure 8B:
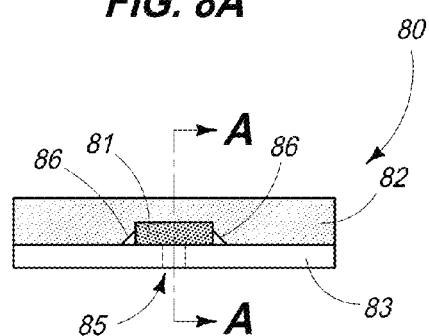

After the epoxy was completely cured, a minimal amount of 100% silicone caulk 86 was carefully applied to the corner created between the MSM element and the glass slide (FIG. 8B). SYLGARD 184 silicone elastomer (available from Dow Corning Corp. in Midland, Mich.) is a liquid before it cures, so the silicone caulk helps seal the working channel so that the elastomer won't leak into it and render the micropump ineffective. The silicone caulk was allowed to cure before preparing the elastomer.

A small piece of electrical tape was placed over the two exposed holes to make sure that the elastomer wouldn't leak into them. Dow Corning 92-023 primer was then painted onto the glass that would be in contact with the elastomer. The primer acts as an adhesive between the elastomer and another surface and, for this reason, contact with the MSM element was avoided. Doing so could suppress local straining of the MSM element.

The prepared micropump was then placed into the center of a polystyrene weigh dish. After thoroughly mixing the Sylgard 184 silicone elastomer as per its instructions, it was poured over the micropump so that the elastomer completely covered it, adding 0.5 mm to the total thickness of the micropump. The weigh dish was set aside and allowed 48 hours to cure at room temperature. Finally, the elastomer was cut to fit the glass plate. Overall the micropump measured 25 mm×10 mm×2.5 mm.

DNA Profiling.

To evaluate use of the micropump in biological testing, the commercially available AmpFlSTR® Identifiler® PCR Reagents kit was used to set up the reactions at a total volume of 25 μl (for the samples having contact with the pump) or 12.5 μl (for the positive and negative controls). Each 25 μl reaction contained 10.5 μl of the AmpFlSTR® PCR Reaction Mix, 5.5 μl of the AmpFlSTR® Identifiler® Primer Set, and 0.5 μl of the AmpFlSTR® Kit AmpliTaq Gold® DNA Polymerase. Those reactions containing only 12.5 μl total volume contained all the listed reagents in exactly half that amount; these were first combined in a master mix, and then distributed in the appropriate amount to each sample tube. The control DNA from the AmpFlSTR® Yfiler™ PCR Reagents kit (cell line 9947A) was used as the sample and positive control DNA, diluted to a final concentration of 0.1 nanogram (ng)/μl; 10 μl of which was added to the full (25 μl) reactions, 5 μl of which was added to the half (12.5 μl) reactions. The negative control had 5 μl of 1× TE (IDT; pH 8.0). All reactions sat incubating at room temperature while the samples were put through the pump.

Four water washes were performed on the pump: first 10 μl, second 15 μl, and the third and fourth 20 μl of nuclease-free water (IDT). Water was added continuously through the pump (hand turning the cylindrical magnet). As the water came off the outlet well, it was wicked off using a Kimwipe™ (Kimberly-Clark). The pump was allowed to dry for approximately 5 minutes, until it was free of visible liquid. Then, the first sample (Pu 1) was added to the inlet well in the same manner as the water, until all 25 μl had been added to the inlet well. Sample was collected from the outlet well 1-2 μl at a time using a micropipette, until all liquid possible was extracted from the pump and placed in a fresh tube. The first 5 μl of Pu 1 were collected and stored separately from the rest of the output, to avoid any potential water carry-over from the earlier washes. The remaining two samples (Pu 2 and Pu 3) were put through the pump one at a time, without any washing of the pump between samples, and collected separately in the same way as Pu 1.

Once all three samples were run on the pump, 12.5 μl was collected from each pump sample tube and placed in a fresh tube for use on the thermal cycler. All samples were vortexed and spun down and placed on a Bio-Rad MJ Mini™ Personal Thermal Cycler using a protocol with the following conditions: 95° C. for 11 min, 28 cycles of 94° C., 59° C., and 72° C. for 1 minute each, and a final step of 60° C. for 1 hour and 30 minutes. After PCR, the samples were loaded on the Applied Biosystems 3130 Genetic Analyzer and the results were examined using GeneMapper® ID-X software.

The commercially available Applied Biosystems Quantifiler® Human DNA Quantification Kit was used with half reactions (12.5 μl volume total: 1 μl DNA (0.1 ng), 6.25 μl Quantifiler™ PCR Reaction Mix, 5.25 μl Quantifiler™ Human Primer Mix); the DNA used for these experiments was the positive control DNA from cell line 9947A (AmpFlSTR® Yfiler Control DNA 9947A at 10 ng/μl) in a 1/100 dilution for a final concentration of 0.1 ng/μl. There were three samples to be treated with the MSM element (RT1, 2, 3), and three positive controls (RPC1, 2, 3) to determine repeatability as well as a negative control (RNC). Samples were placed in an Applied Biosystems MicroAmp® Optical 96-Well Reaction Plate, where the MSM element was placed in the well of each RT sample for 10 minutes at a time. Elements that were re-used were cleaned with 10% bleach and 70% EtOH. Once all incubations were complete, the plate was sealed with an Applied Biosystems MicroAmp® Optical Adhesive Film and was centrifuged at 3000 rpm for 1 minute before loading onto the Eppendorf Mastercycler® ep Realplex 4. PCR conditions used were those recommended in the Quantifiler® Human Kit Manual: 50.0° C. for 2 minutes, 95.0° C. for 10 minutes, and then 40 cycles of 95.0° C. for 15 sec followed by 60.0° C. for 1 min. The Quantifiler® kit uses a dual hybridization Taqman® probe whose target gene is human telomerase reverse transcriptase (hTERT), the reporter dye being FAM. Standards were run in duplicate on the plate with the samples as recommended by Applied Biosystems in the kit manual using the concentrations listed therein. Results were analyzed using the realplex software, and a standard curve was produced, after eliminating one standard at each of the following concentrations: 0.068 ng/µl and 0.023 ng/µl, with a slope of −3.300, a Y-intercept of 28.91, and R2 value of 0.996.

No Loss of DNA after MSM Pumping.

The PCR amplification and final forensic profiles obtained from PCR reactions incubated for 10 minutes with the MSM element, the elastomer, and the silicone components of the pump assembly were assessed. While the silicone and, to a lesser degree the elastomer, had some negative impact on PCR (data not shown), Ni—Mn—Ga, the material of the pump element, enhanced amplification significantly. Encouraged by this, the assembled pump was used to assess its impact on PCR and profile quality. Six samples were prepared of human genomic DNA in water (0.1 ng/µl) with Quantifiler reaction mix and primers; three of the samples were incubated for 10 minutes with Ni—Mn—Ga at room temperature, and three were left at room temperature as controls; a seventh reaction served as a reagent control, and had no genomic DNA. All samples were prepared in a 96-well plate, and amplified according to the manufacturer's guidelines. The samples that were incubated with the Ni—Mn—Ga amplified as well or better than the standard reaction controls, indicating that the alloy did not decrease the measureable amount of DNA in aqueous solution, and that it did not produce a net negative effect on DNA amplification.

Enhanced Forensic Profiling Following MSM Pumping.

Six PCR amplification reactions with genomic DNA (and one reagent control with no template DNA) in 0.2 ml plastic tubes were prepared according to the Identifier instructions. Three of the reactions with genomic DNA were run through the constructed micropump before placing them in new tubes. The remaining tubes were left at room temperature during this time. All 7 reactions were then placed in a thermocycler for amplification. We followed kit manufacturer's recommendation for all cycling parameters, using 0.5 ng of the kit's genomic control DNA in a 12.5 µl total reaction volume.

The Identifier results showed that PCR reactions run through the pump were significantly enhanced. For each allele, the relative fluorescence units (RFU) areas were higher in the pumped (Pu) samples. In all experiments to date, PCR reactions that pass through the pump yield DNA profiles with higher DNA peaks than those that do not go through the pump.

Example 1 above demonstrates the design and use of a micropump, essentially made from a single component, a Ni—Mn—Ga MSM element. The pump was compatible with biological testing, and increased PCR yield in forensic profiling. An added benefit of the constructed pump and like micropumps described herein may include not requiring any electrical or physical contact with the pump driver, therefore allowing a sealed and disposable component for clinical and field applications. Investigators operated the driving magnet by hand in all of the experiments shown here, but also demonstrated more rapid pumping achieved using an electric drill motor at 1000 RPM. Thus, the micropumps herein may be suitable for field operations where power is unavailable (or undesirable), and where sealed disposable units are beneficial. Lab-on-a-chip designs with multiple, independent MSM pumps are conceivable, as are PCR enhancers based on the MSM material.

A clear benefit exists in using materials that catalyze (or enhance) reactions when building pTAS components. Ni—Mn—Ga offers increased PCR amplification and has other diverse properties that make it promising for an array of microdevice components. Its capacity to transduce charge, motion, and current make it ideal for actuators, energy harvesters, and a variety of measuring devices. Finally, biological/metal hybrids have been constructed using other metal catalysts, but hybrids of Ni—Mn—Ga may combine the unique sensing and motility characteristics of Ni—Mn—Ga with the established biological properties of biomolecules, such as substrate specificity and biological catalysis.

In a further embodiment, a micropump includes at least one MSM element containing a material configured to expand and/or contract in response to exposure to a magnetic field. A device is configured to generate a magnetic field, the MSM element being configured to pump fluid through the micropump by expanding and/or contracting in response to the magnetic field.

By way of example, the micropump may include the features described above for the actuation apparatus embodiment. Accordingly, the MSM element may be configured to contract and/or expand locally in response to local exposure to the magnetic field. A magnet alignment device may be configured to restrain magnet movement to rotation about an axis of rotation. The magnetic field distribution may have a component substantially perpendicular to the axis of rotation. The at least one MSM element may be between two parallel plates and be sealed within the plates except for an inlet to the MSM element and an outlet from the MSM element.

In a still further embodiment, a PCR enhancement method includes using a PCR reagent combined with a DNA material and contacting the PCR reagent and DNA material with a magnetic shape memory (MSM) element. The method includes amplifying the DNA material, the amplification being greater than would occur in the method without the PCR reagent and DNA material contacting the MSM element.

By way of example, the contact with the MSM element may include placing the MSM element in the combined PCR reagent and DNA material. Instead, or additionally, the contact with the MSM element may include pumping the combined PCR reagent and DNA material through a micropump using the MSM element.

Accordingly, a micropump may transfer fluid in shrinkage of an element of an MSM material, driven along the element by the alternating magnetic field of a rotating diametrically magnetized magnet. The unique magnetic field distribution may affect the magnetic shape memory element in parallel and perpendicular directions of the element at the same time in different locations of the element. In those locations of the element where the field is in perpendicular direction, the element may shrink in the perpendicular direction (element becomes thinner locally). In those locations where the field is in parallel direction, the element may expand in the perpendicular direction (element becomes thicker locally). By rotating the diametrically magnetized magnet, or by generating a similar magnetic field configuration by other means, the shrinkage travels along the element. If the element is placed between two parallel plates and sealed in the sides, the shrinkage may transfer fluid along the element.

The sides of the element may be sealed using an elastic resin, and the back side of the element covered with an elastomer. The elastomer also presses the element against the cover plate (including the inlet and outlet holes), thus stabilizing the thin twin structure for operation of the pump. Recent developments in manufacturing of Ni—Mn—Ga single crystals and elements in the laboratory made the micropump development possible. Quality MSM elements with low twinning stress and thin twin structure were successfully made and used for the operation of the micropumps.

The MSM micropump herein provides the advantage of being simpler, more precise in dosing, faster in pumping, and less expensive than known micropumps. The pump may be wireless, that is, powered by external magnetic field sources. The MSM micropump can pump in both directions and it does not need valves.

MSM micropumps seem to be suitable for lab-on-a-chip diagnostics devices. The microfluidic market is expected to grow from 1600 million dollars to 3000 million dollars in the next three years. There has been a shortage of proper micropumps in the microfluidic device. Multi-axial magnetic field configurations for micropumps are not currently known. Even though U.S. Pat. No. 6,074,179 describes a magnetostrictive material expanding directionally in the presence of a magnetic field in a peristaltic pump, the local magnetic fields generated by coils are merely unidirectional.

For the embodiments herein, MSM materials produce large (up to 10% of the length of the sample) and fast (rise time less than 0.1 millisecond) strains with high position accuracy in an applied magnetic field. An external magnetic field powers the MSM pump. Therefore, the device is wireless and contact-free, so the entire pump and lab-on-a-chip are inexpensive and disposable. The MSM micropumps are simple. MSM material is placed in a microfluidic channel and acts as the pumping mechanism. These pumps achieve a high dosing accuracy, and volumes can be scaled from nanoliters to milliliters. This is due to the high position accuracy of the MSM materials, and the high cycling frequency the MSM pumps. This large dynamic range is not possible to achieve with any other technology.

Two hypothetical examples follow on the principles demonstrated in Example 1 above, a biomimetic "swallow" pump and, to a lesser extent, a three-element plunge pump. The plunge pump may include programmed strokes of three plunges made of MSM elements to perform pumping. Dosing accuracy is estimated at 10 nanoliters (nl) and maximum flow at 1 ml/min. The swallow pump provides a swallow wave that travels along the MSM element, allowing the magnetic field to pump the fluid. Dosing accuracy is estimated at 1 nl-10 nl and maximum flow at 50-500 µl/min. The pumps may be powered by magnetic field pulses generated by small coils, but the use of only rotating permanent magnets may be suitable.

Figure 9:
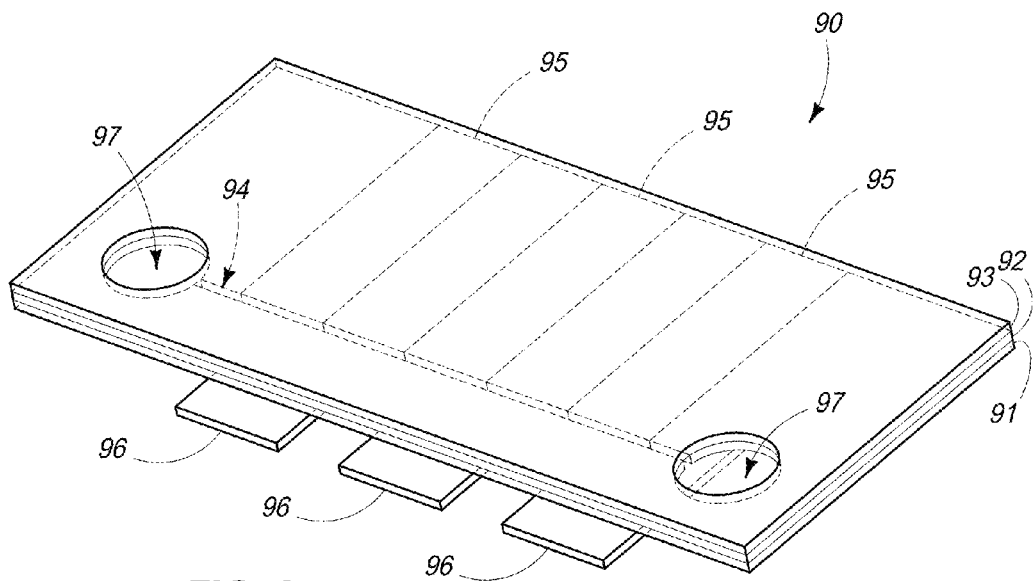
FIG. 9 is a perspective view of selected components of a three-element plunge micropump.

As in FIG. 9, three-element micropump 90 is composed of three plates 91, 92, and 93, possibly glass, of 0.2 mm in thickness welded together using a laser. Plates 91, 92, and 93 are shown in FIG. 9 as transparent to see internal structures; however, they may instead be opaque. A fluid channel 94 (0.2 mm wide) and three pumping MSM elements 95 are placed in between two glass plates. Pumping elements 95 may be MSM material (0.2×2×6 mm$^3$) that elongate 6% of their length in a magnetic field (perpendicular to the plate), and shrink 6% in a magnetic field directed parallel to the long dimension of the element. Magnetic field sources 96 may be placed adjacent MSM elements 95 to effectuate operation of micropump 90. Fluid enters and exits fluid channel 94 through openings 97 in plates 93 and 92.

Figure 10:
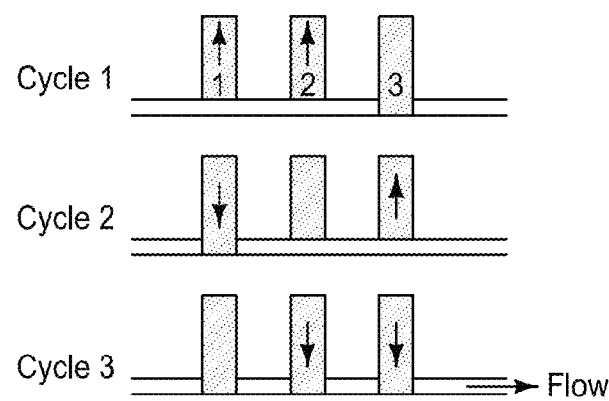
FIG. 10 shows operation cycles of the FIG. 9 micropump.
Figure 11:
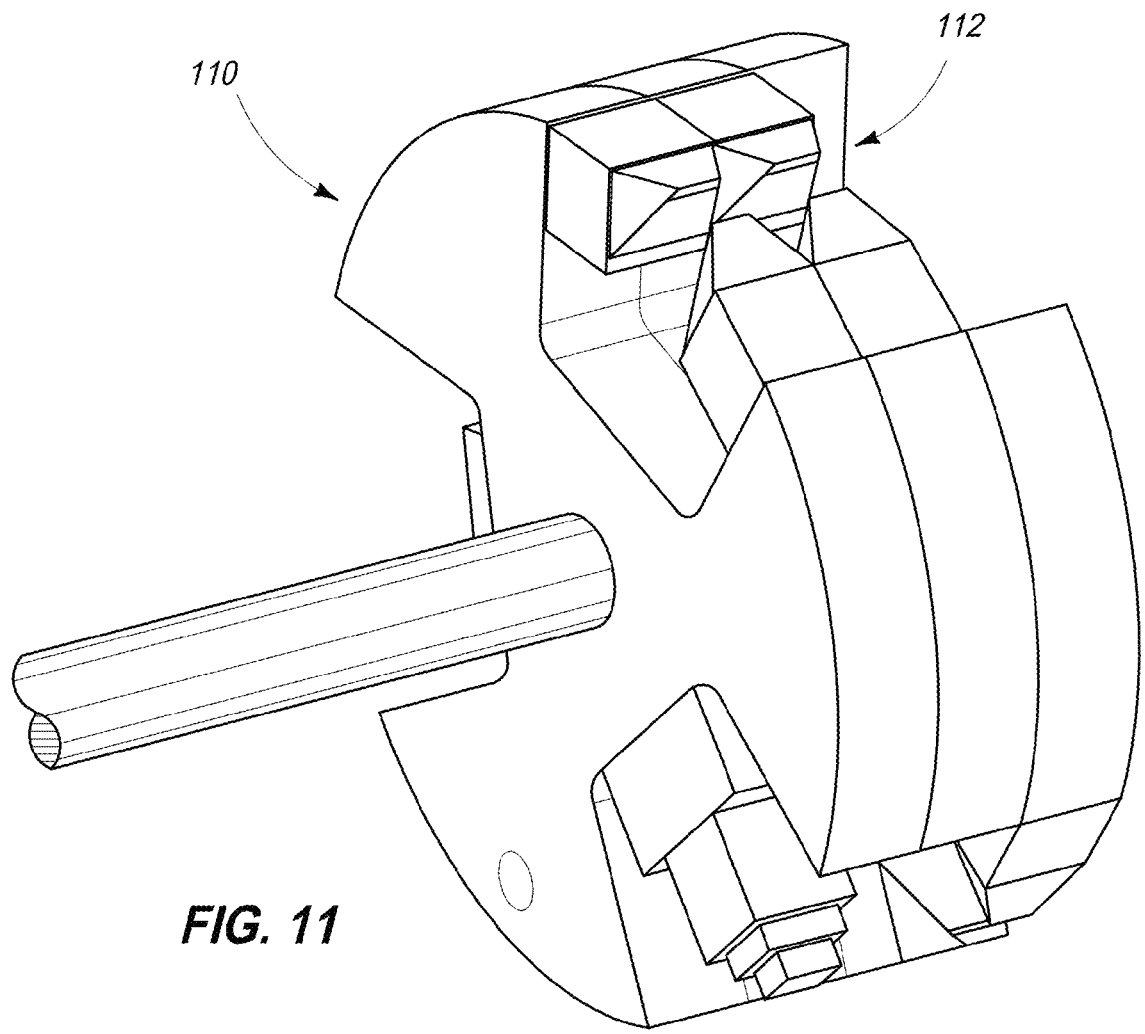
FIGS. 11 and 12 are perspective views of wheel-mounted magnets for use with the FIG. 9 micropump.
Figure 12:
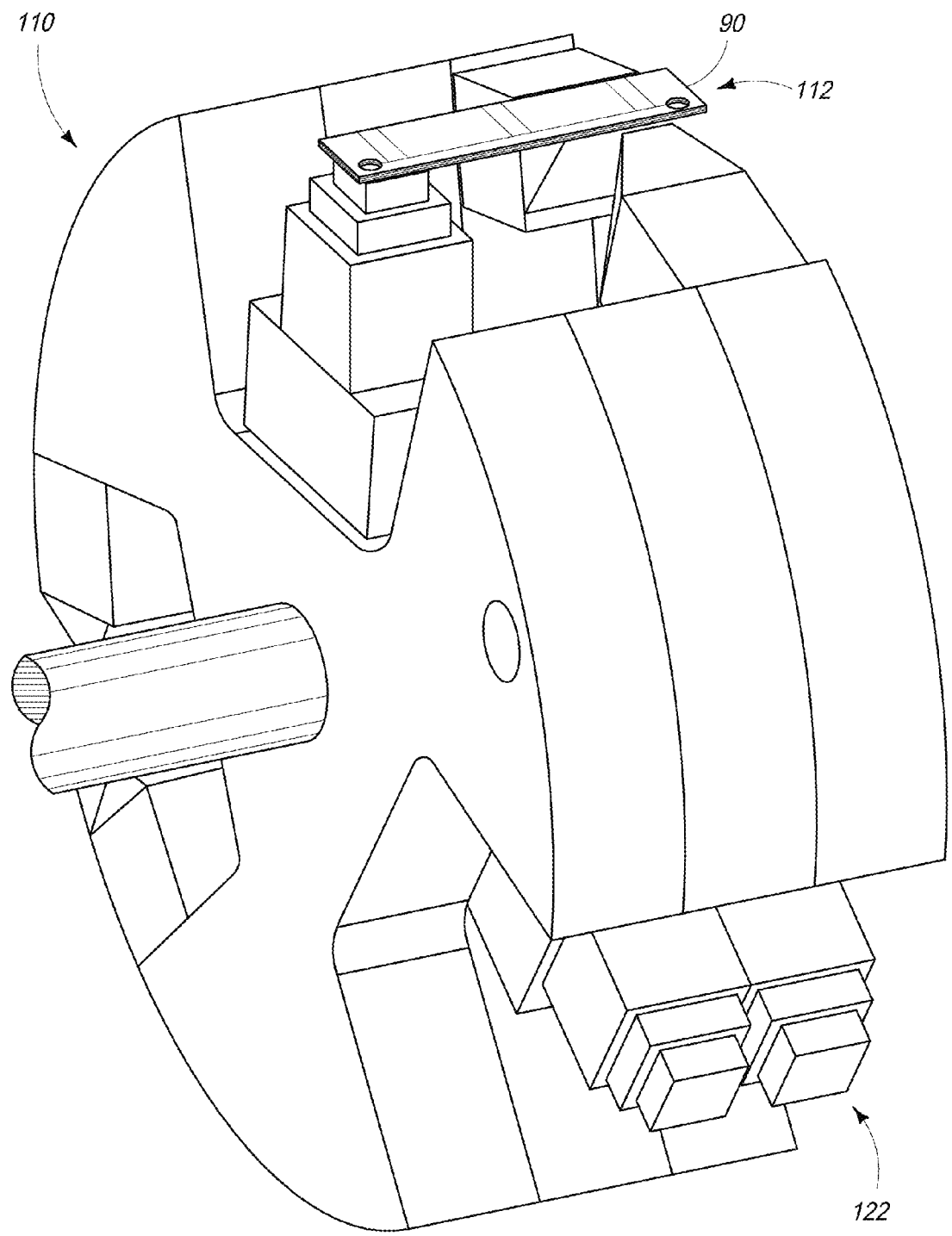

As in FIGS. 11 and 12, a wheel 110 may rotate underneath micropump 90 and contain three sets of magnets that generate magnetic fields parallel and perpendicular to the long dimension of MSM elements 95. Parallel fields elongate the elements and perpendicular fields shrink the elements, thus generating the pumping cycles shown in FIG. 10. Magnet set 112 generates two parallel fields causing the first and second element to shrink in Cycle 1 of FIG. 10. The shrinking elements allow fluid into channel 94. Magnet set 120 generates one perpendicular field and one parallel field causing the first element to elongate and third element to shrink in Cycle 2. The elongating first element closes channel 94 from back flow and the shrinking third element opens channel 94 to forward flow. Magnet set 122 generates two perpendicular fields causing the second and third element to elongate in Cycle 3. The elongating second and third elements push fluid forward from channel 94. A return to Cycle 1 begins the process again.

Merely rotating wheel 110 will be appreciated to establish the three cycles of FIG. 10. Also, wheel 110 produces a magnetic field distribution including at least two components substantially orthogonal to one another lying in one or more planes perpendicular to the axis of rotation and one of the orthogonal components includes the component substantially perpendicular to the axis of rotation. Also, individual ones of the orthogonal components lie in different planes perpendicular to the axis of rotation.

Figure 13:
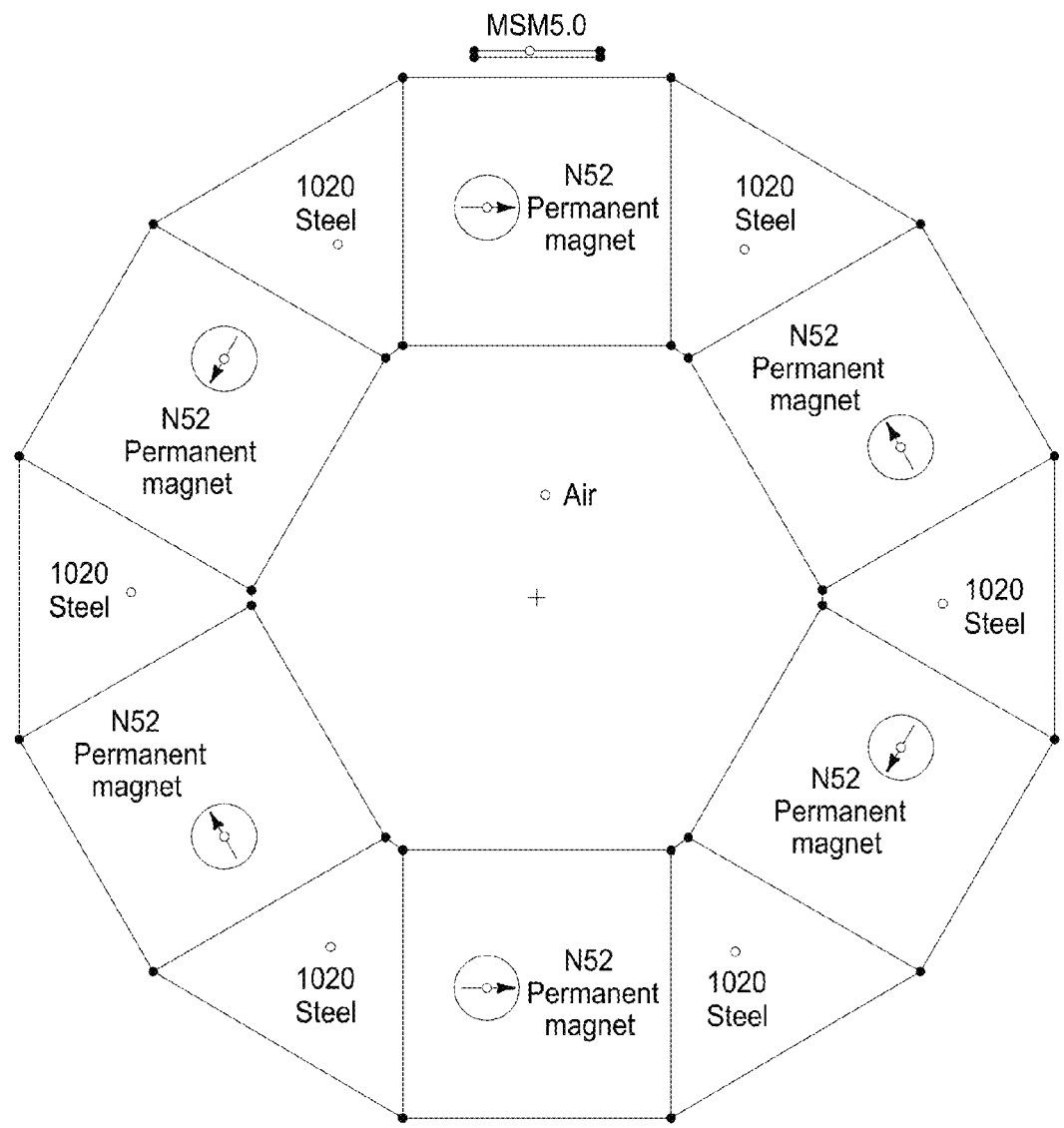
FIGS. 13-18 show designs for wheel-mounted magnets as alternatives to the FIGS. 11 and 12 device.
Figure 14:
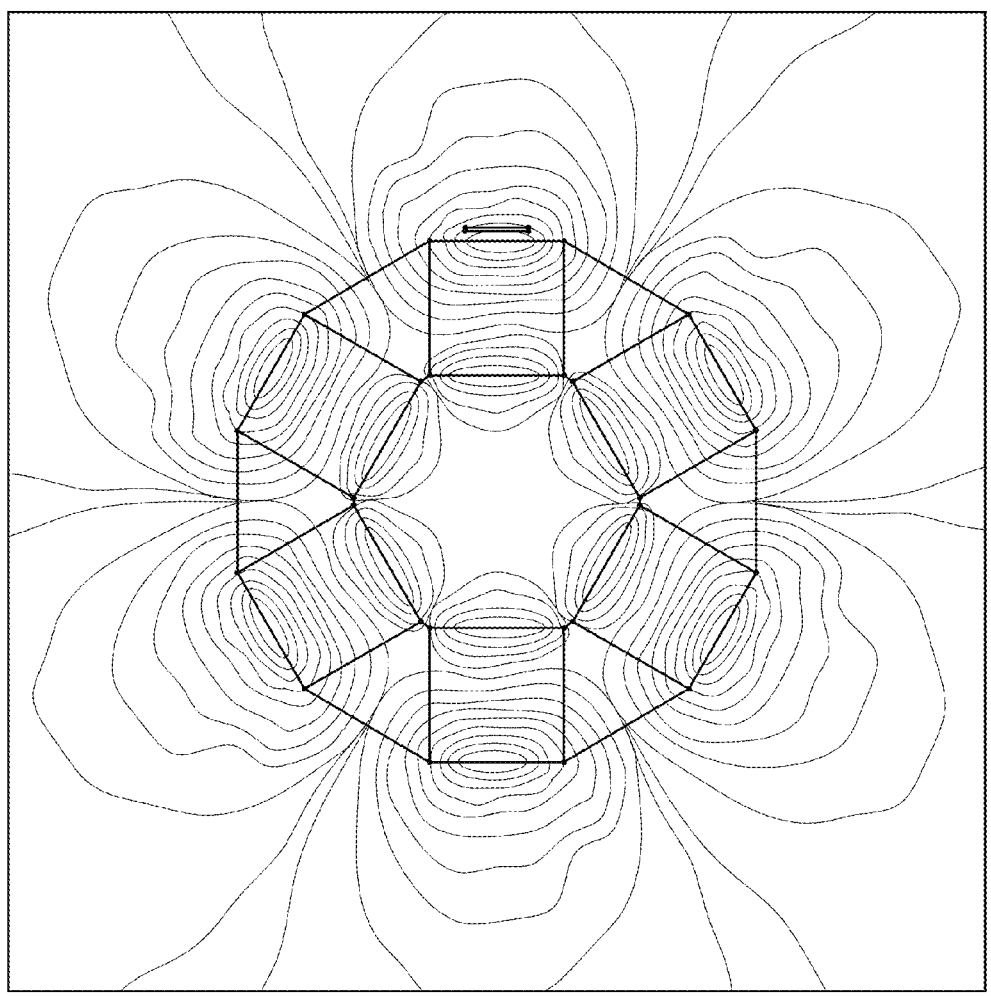
Figure 15:
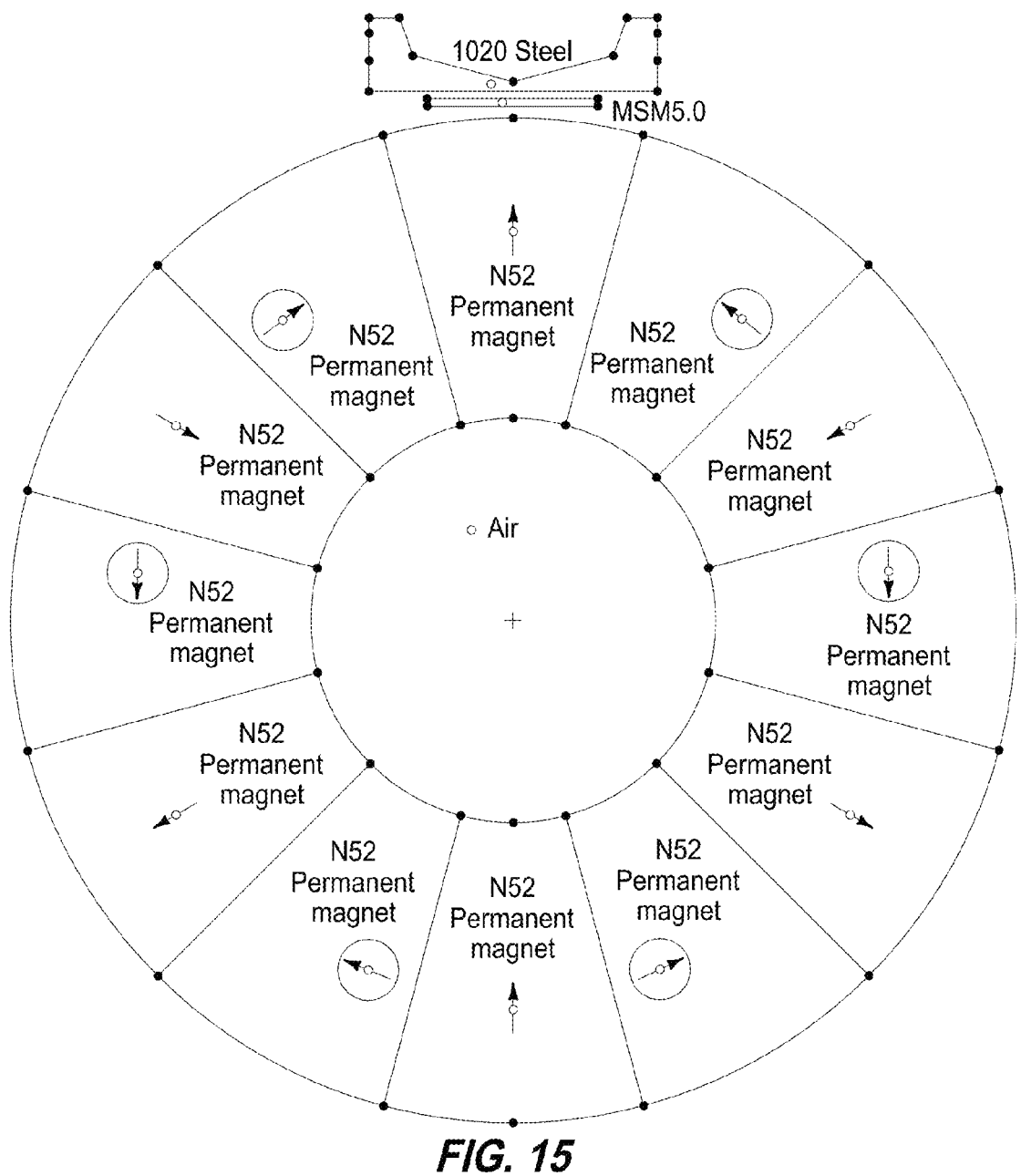
Figure 16:
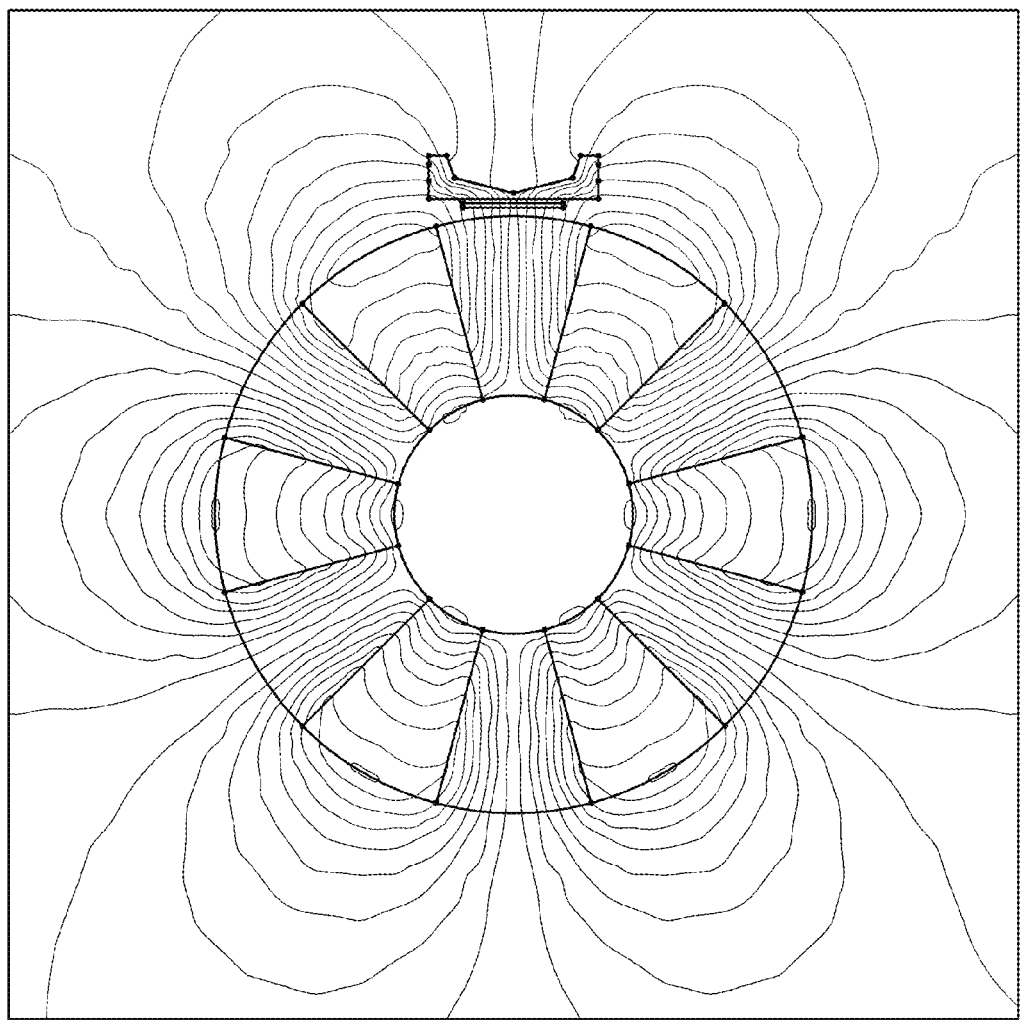
Figure 17:
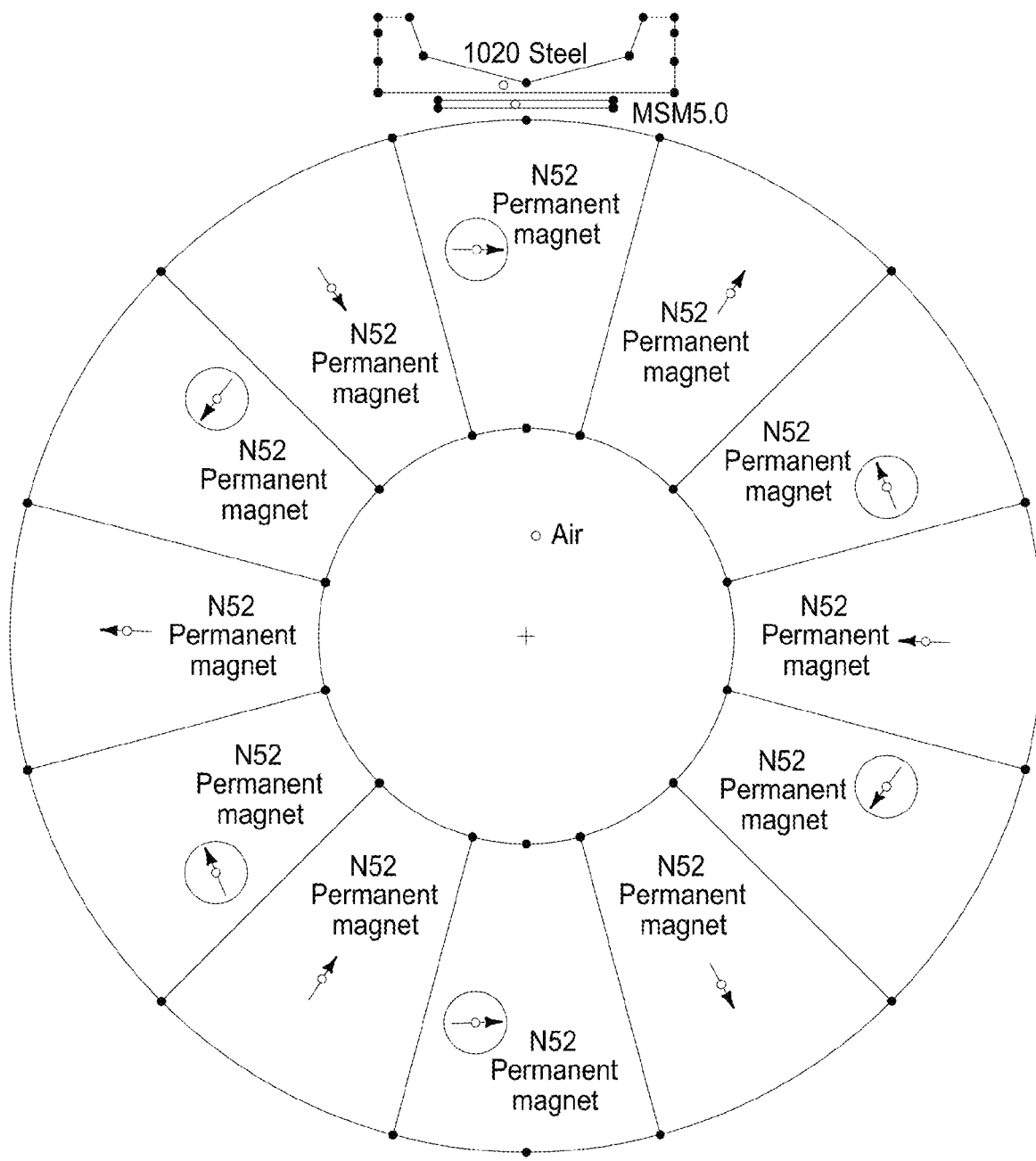
Figure 18:
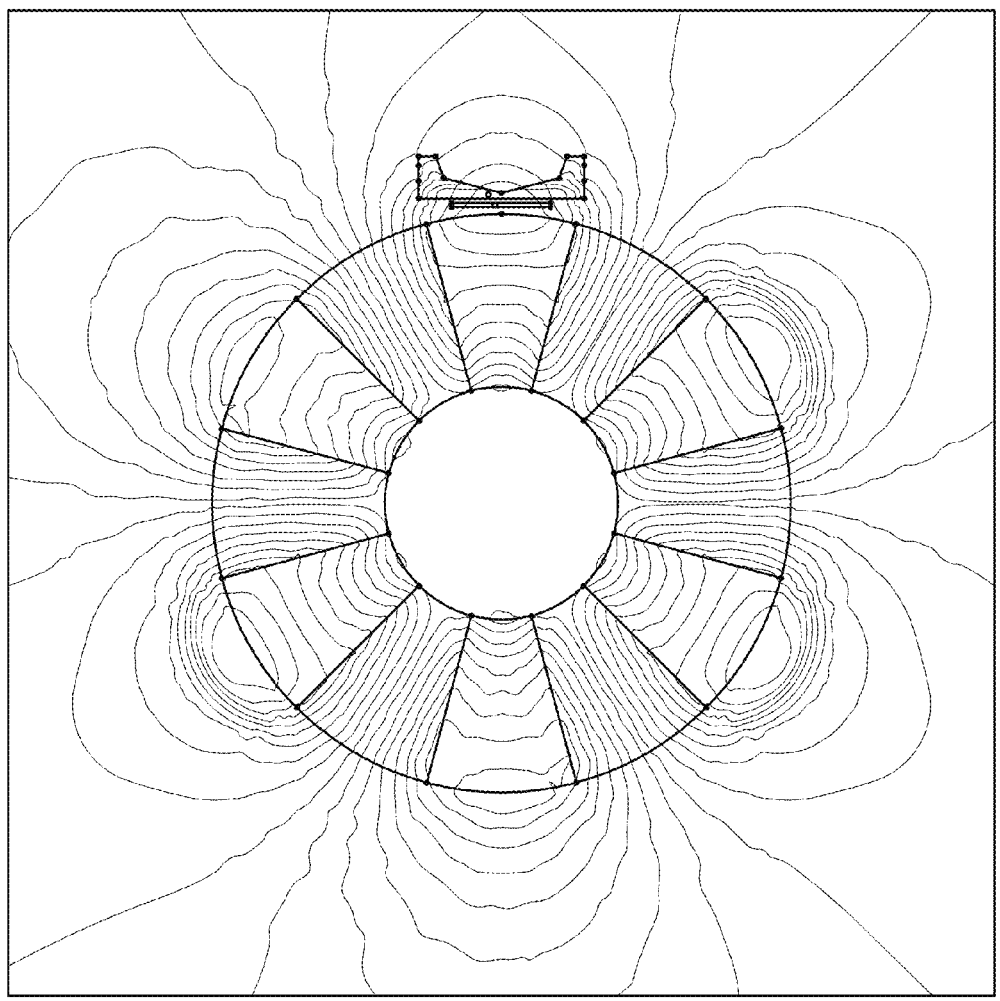

Although the configurations for magnets shown in FIGS. 11 and 12 have been modeled to provide the desired magnetic fields, other magnet configurations are conceivable. For example, FIG. 13 shows a combination of permanent magnet squares in the orientations shown and triangle-shaped low carbon steel pieces. The FIG. 13 wheel produces the magnetic field distribution of FIG. 14 with perpendicular and parallel components. FIGS. 15 and 17 show a Halbach rotor combined with a steel focuser placed above the micropump to produce homogeneous perpendicular and parallel magnetic fields. The FIGS. 15 and 17 wheels produce the magnetic field distributions of FIGS. 16 and 18.

Figure 19:
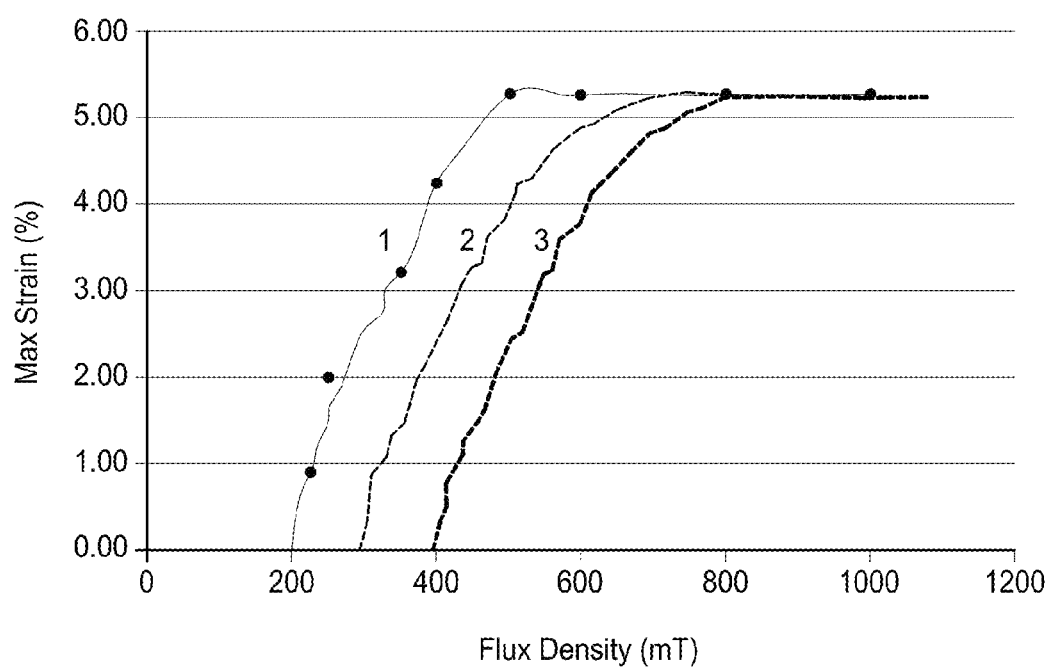
FIG. 19 is a chart of flux density versus maximum strain for three different MSM elements.

As an alternative to the wheel designs described above, a method for straining several MSM elements in different phases by a rotating cylindrical magnet is conceivable. A rotating diametrically magnetized cylindrical magnet produces a gradually increasing and decreasing magnetic field when the cylinder rotates. Different MSM elements can experience different strains at different, controlled time intervals. FIG. 19 shows three strain vs. magnetic flux density curves. The element 1 curve starts straining at 200 milliTesla (mT). The first element of micropump 90 shown in FIG. 9 may be made from that material. The second and third elements of micropump 90 may be made from material exhibiting the behavior shown in FIG. 19 for elements 2 and 3, respectively. When the cylindrical magnet rotates underneath the three MSM elements, element 1 strains first, once the flux density reaches 200 mT. After that, element 2 strains when the flux density is 300 mT. Element 3 strains last when the flux density has reached 400 mT. Difference in the flux densities (switching fields) of the MSM elements makes the intervals of straining of the elements.

There are several ways to increase switching field, for instance, by coating the surfaces of the MSM elements with titanium nitride (TiN). Element 1 could be uncoated, element 2 coated with a 50 nm thick TiN layer, and element 3 coated with a 200 nm thick TiN layer. Coating increases twinning stress and switching field. Other ways to increase switching field are surface deformations or other treatments, heat treatments, compositional changes, and spring loading of the elements. If a desire exists to change the order of strokes in parallel fields as compared to perpendicular fields, elements can be placed in bias magnetic fields of different fields strengths. Bias field decreases switching field when the applied field is along switching field, but increases switching field in perpendicular direction. Using bias magnets, opposite directions of the magnetic fields can also be made unsymmetrical. For instance, the field in north direction can strain the sample, but south direction does not strain, if the bias magnet increases the field in the north direction.

Figure 20:
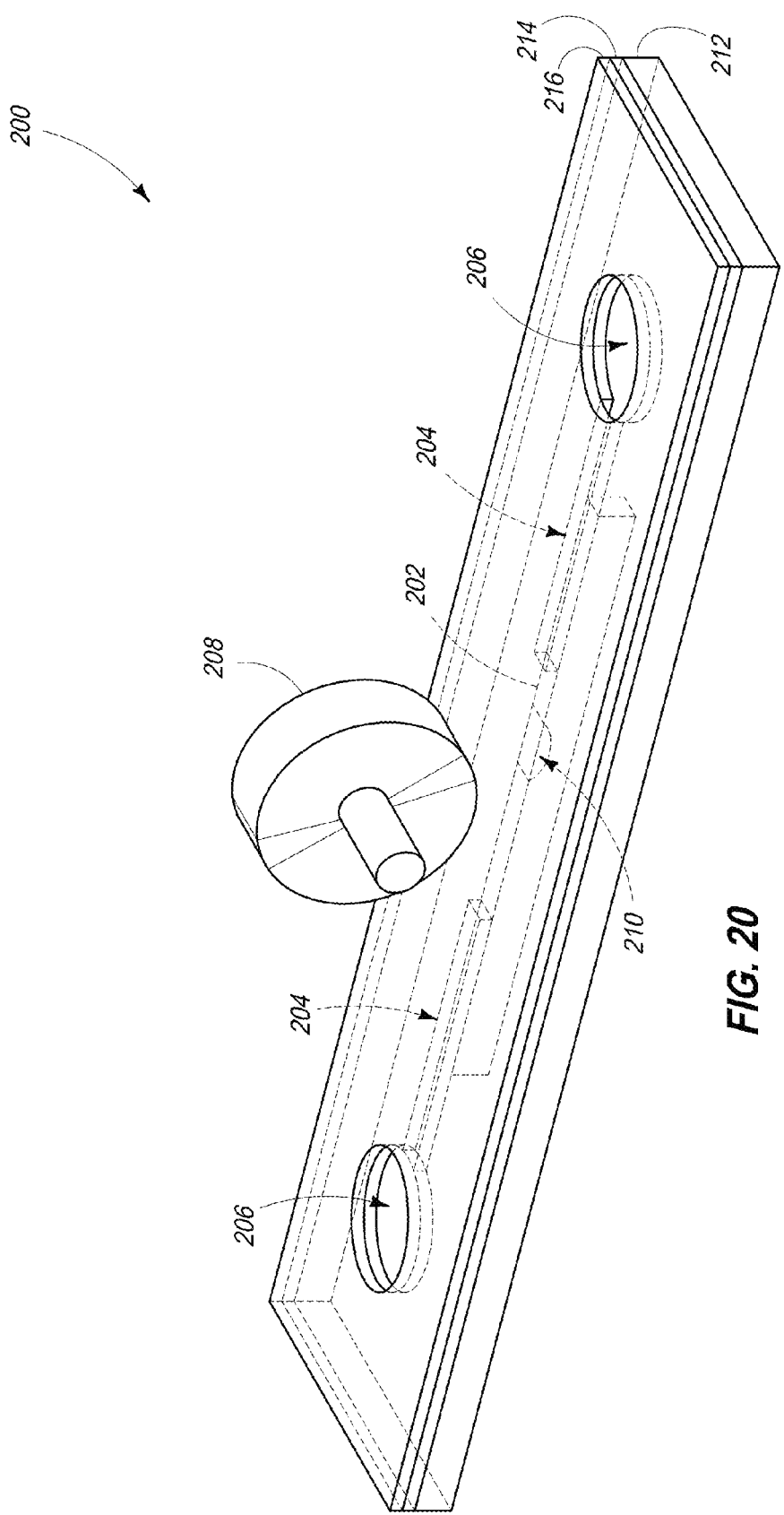
FIG. 20 is perspective view of selected components of a swallow micropump.
Figure 22:
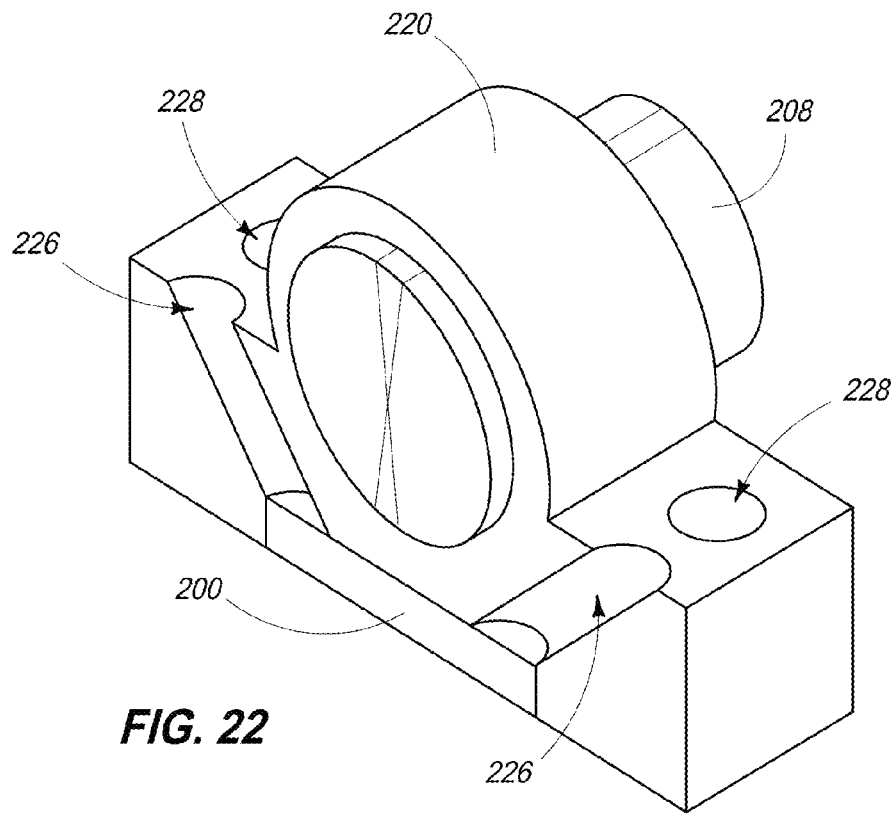
FIG. 22 is a perspective view of selected components of a swallow micropump.

The swallow pump introduced above and shown in FIG. 20 functions analogously to the micropump demonstrated in Example 1. Advantageously, it can be made thin enough to be placed inside a microfluidic lab-on-a-chip device. For example, pump 200 may be 0.9 mm thick using plates 212, 214, and 216 and MSM element 202 may be 0.5 mm thick. Plates 212, 214, and 216 are shown as transparent; however, they may be opaque. Fluidic channels 204 connecting openings 206 may be 0.5 mm wide and 0.2 mm deep. Pump 200 is powered by a rotating magnet 208 placed above the pump. Pump 200 has no contact with the magnetic or any electrical source. FIG. 22 shows one example of a magnet alignment device 220. The FIG. 22 device may be used in conjunction with pump 200 shown in FIG. 20 or with other like pumps. Device 220 includes openings 226 that may align with openings 206 in the top plate of pump 200. Holes 228 may be used to bolt device 220 to pump 200.

Figure 21:
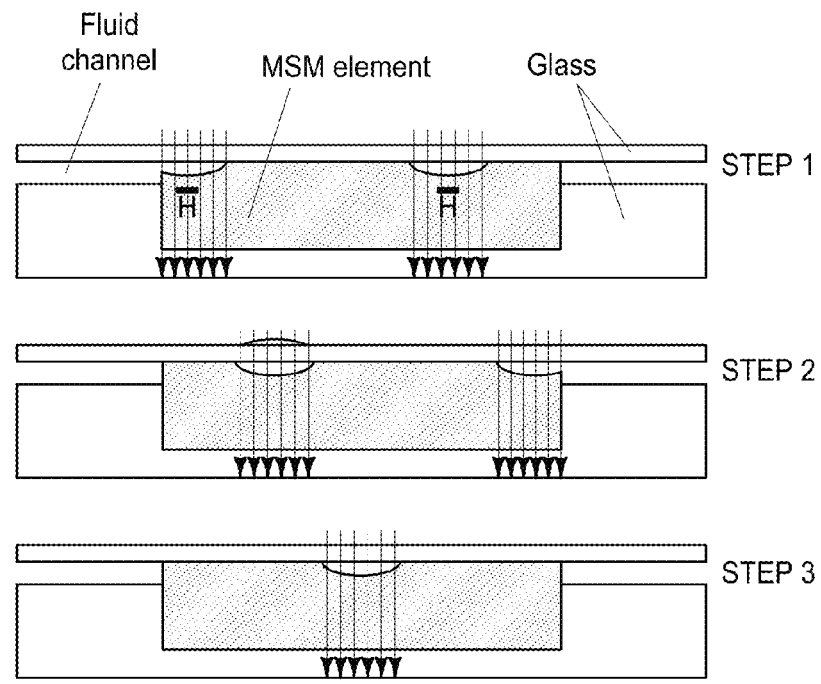
FIG. 21 shows operation steps of the FIG. 20 micropump.

The swallow pump is based on biological models of movement. MSM element 202 shrinks locally in the direction of the applied magnetic field. Just as in muscular contraction, the element shrinks locally in one direction (gets thinner), and grows in the other (gets longer). A traveling local magnetic field moves along MSM element 202 from left to right in FIG. 20. The moving field carries shrinkage 210 that transfers fluid. FIG. 21 shows three snapshots, Steps 1 to 3, of the pumping process.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

The invention claimed is:

1. An actuation method comprising:
   rotating a magnetic field about an axis of rotation;
   exposing magnetic shape memory (MSM) material comprised by at least one MSM element to different portions of the magnetic field as a result of rotating the magnetic field, the MSM material having a dimension; and
   contracting the MSM material locally across the dimension in a first part of the MSM material in response to local exposure to a first component of the magnetic field substantially parallel to the dimension while simultaneously not contracting the MSM material locally in a second part exposed to a second component of the magnetic field not substantially parallel to the dimension, the contracted first part of the MSM material being located at a position within the magnetic field of sufficient flux density to produce the local contraction and the not-contracted second part of the MSM material also being located at such a position, but not contracting due to the not substantially parallel direction of the second component.

2. The method of claim 1 further comprising, as a result of the rotating, subsequently moving a location where the MSM material is exposed to a component of the magnetic field substantially parallel to the dimension and, correspondingly, moving a location of a locally contracted part of the MSM material.

3. The method of claim 1 wherein the at least one MSM element comprises nickel, manganese, and gallium.

4. The method of claim 1 wherein the at least one MSM element consists of nickel, manganese, and gallium.

5. The method of claim 1 wherein rotating the magnetic field comprises rotating at least one permanent magnet.

6. The method of claim 5 wherein the at least one permanent magnet comprises a diametrically magnetized magnet.

7. The method of claim 1 wherein the first and second components of the magnetic field are substantially orthogonal to one another lying in one or more planes perpendicular to the axis of rotation and the second component not substantially parallel to the dimension is thus substantially perpendicular to the dimension.

8. The method of claim 7 wherein the at least one MSM element consists of one MSM element, the orthogonal components lie in the same plane perpendicular to the axis of rotation, and the dimension is a thickness of the MSM element, which is less than a length of the MSM element.

9. The method of claim 7 wherein:
   the at least one MSM element comprises a plurality of MSM elements, the first and second orthogonal components lie in different planes perpendicular to the axis of rotation, and the dimension is a length of individual MSM elements, which is greater than a thickness of individual MSM elements;
   the first part of the MSM material comprises a first MSM element and the second part of the MSM material comprises a separate, second MSM element;
   simultaneously not contracting the second part of the MSM material comprises simultaneously expanding the second MSM element along the length in response to exposure to the second component of the magnetic field substantially perpendicular to the length; and
   the method further comprises, as a result of the rotating, subsequently changing which of the plurality of MSM elements is exposed to a component of the magnetic field substantially parallel to the length and, correspondingly, contracting the second MSM element along the length.

10. The method of claim 1 further comprising pumping fluid through a micropump using the contracting.

11. The method of claim 1 further comprising:
   using a polymerase chain reaction (PCR) reagent combined with a DNA material;
   contacting the PCR reagent and DNA material with the MSM element; and
   amplifying the DNA material, the amplification being greater than would occur in the method without the MSM element contacting the PCR reagent and DNA material.

12. An actuation apparatus comprising:
   at least one permanent magnet exhibiting a magnetic field;
   a magnet alignment device configured to restrain magnet movement to rotation about an axis of rotation; and magnetic shape memory (MSM) material having a dimension and being comprised by at least one MSM element, the MSM material containing a combination of nickel, manganese, and gallium configured to contract locally across the dimension in a first part of the MSM material in response to local exposure to a first component of the magnetic field substantially parallel to the dimension, but also configured not to contract locally in a second part simultaneously exposed to a second component of the magnetic field not substantially parallel to the dimension, the first part of the MSM material being located at a position within the magnetic field of sufficient flux density to produce the local contraction and the second part of the MSM material also being located at such a position, but not contracting due to the not substantially parallel direction of the second component.

13. The apparatus of claim 12 further comprising a magnet rotation device configured to move a location where the MSM material is exposed to a component of the magnetic field substantially parallel to the dimension and, correspondingly, configured to move a location of a locally contracted part of the MSM material.

14. The apparatus of claim 12 wherein the at least one permanent magnet comprises a diametrically magnetized magnet.

15. The apparatus of claim 12 wherein the at least one permanent magnet comprises a wheel mounted with at least six permanent magnets.

16. The apparatus of claim 12 wherein the first and second components of the magnetic field distribution are substantially orthogonal to one another lying in one or more planes perpendicular to the axis of rotation and the second component not substantially parallel to the dimension is thus substantially perpendicular to the dimension.

17. The apparatus of claim 16 wherein the at least one MSM element consists of one MSM element, the orthogonal components lie in the same plane perpendicular to the axis of rotation, and the dimension is a thickness of the MSM element, which is less than a length of the MSM element.

18. The apparatus of claim 16 wherein:
the at least one MSM element comprises a plurality of MSM elements, the first and second orthogonal components lie in different planes perpendicular to the axis of rotation, and the dimension is a length of individual MSM elements, which is greater than a thickness of individual MSM elements;
the first part of the MSM material comprises a first MSM element and the second part of the MSM material comprises a separate, second MSM element;
the second part of the MSM material configured not to contract is configured to expand along the length in response to exposure to the second component of the magnetic field substantially perpendicular to the length; and
the apparatus further comprises a magnet rotation device configured, as a result of the rotating, to change which of the plurality of MSM elements is exposed to a component of the magnetic field substantially parallel to the length and, correspondingly, to contract the second MSM element along the length.

19. A micropump comprising:
magnetic shape memory (MSM) material having a dimension and being comprised by at least one MSM element, the MSM material containing a material configured to contract locally across the dimension in a first part of the MSM material in response to local exposure to a first component of a magnetic field substantially parallel to the dimension, but also configured not to contract locally in a second part simultaneously exposed to a second component of the magnetic field substantially perpendicular to the dimension, the first part of the MSM material being located at a position within the magnetic field of sufficient flux density to produce the local contraction and the second part of the MSM material also being located at such a position, but not contracting due to the not substantially parallel direction of the second component;
a device configured to generate the magnetic field, the magnetic field generating device including at least one permanent magnet, the MSM element being configured to pump fluid through the micropump at least by contracting in response to the magnetic field; and
a magnet alignment device configured to restrain magnet movement to rotation about an axis of rotation, the at least one permanent magnet exhibiting the magnetic field having the first and second components substantially orthogonal to one another lying in one or more planes perpendicular to the axis of rotation.

20. The micropump of claim 19 further comprising a magnet rotation device configured to move a location where the MSM material is exposed to a component of the magnetic field substantially parallel to the dimension and, correspondingly, configured to move a location of a locally contracted part of the MSM material.

21. The micropump of claim 19 wherein the at least one MSM element comprises nickel, manganese, and gallium.

22. The micropump of claim 19 wherein the at least one MSM element consists of nickel, manganese, and gallium.

23. The micropump of claim 19 wherein the at least one permanent magnet comprises a diametrically magnetized magnet.

24. The micropump of claim 19 wherein the at least one permanent magnet comprises a wheel mounted with at least six permanent magnets.

25. The micropump of claim 19 wherein the at least one MSM element consists of one MSM element, the orthogonal components lie in the same plane perpendicular to the axis of rotation, and the dimension is a thickness of the MSM element, which is less than a length of the MSM element.

26. The micropump of claim 19 wherein:
the at least one MSM element comprises a plurality of MSM elements, the first and second orthogonal components lie in different planes perpendicular to the axis of rotation, and the dimension is a length of individual MSM elements, which is greater than a thickness of individual MSM elements;
the first part of the MSM material comprises a first MSM element and the second part of the MSM material comprises a separate, second MSM element;
the second part of the MSM material configured not to contract is configured to expand along the length in response to exposure to the second component of the magnetic field substantially perpendicular to the length; and
the apparatus further comprises a magnet rotation device configured, as a result of the rotating, to change which of the plurality of MSM elements is exposed to a component of the magnetic field substantially parallel to the length and, correspondingly, to contract the second MSM element along the length.

27. The micropump of claim 19 wherein the at least one MSM element is disposed between two parallel plates and is sealed within the plates except for an inlet to the MSM element and an outlet from the MSM element.

* * * * *

UNITED STATES PATENT AND TRADEMARK OFFICE
CERTIFICATE OF CORRECTION

PATENT NO.         : 9,091,251 B1
APPLICATION NO.    : 13/550386
DATED              : July 28, 2015
INVENTOR(S)        : Kari Ullakko et al.

Page 1 of 1

It is certified that error appears in the above-identified patent and that said Letters Patent is hereby corrected as shown below:

Title Page

(75) Inventors Should Read: Kari Ullakko, Savolinna, Finland (FI);
Peter Mullner, Boise, ID (US);
Greg Hampikian, Boise, ID (US);
Aaron Smith, Meridian, ID (US)

Signed and Sealed this
Twenty-second Day of December, 2015

Michelle K. Lee
*Director of the United States Patent and Trademark Office*